(12) United States Patent
Keller

(10) Patent No.: US 9,254,224 B2
(45) Date of Patent: *Feb. 9, 2016

(54) OPHTHALMIC SURGICAL DEVICE FOR CAPSULOTOMY

(71) Applicant: Mynosys Cellular Devices, Inc., Fremont, CA (US)

(72) Inventor: Christopher Guild Keller, El Cerrito, CA (US)

(73) Assignee: Mynosys Cellular Devices, Inc., Fremont, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/694,473

(22) Filed: Apr. 23, 2015

(65) Prior Publication Data

US 2015/0223980 A1  Aug. 13, 2015

Related U.S. Application Data

(63) Continuation of application No. 14/106,603, filed on Dec. 13, 2013, which is a continuation of application (Continued)

(51) Int. Cl.
*A61B 18/12* (2006.01)
*A61F 9/007* (2006.01)
(Continued)

(52) U.S. Cl.
CPC ............ *A61F 9/00754* (2013.01); *A61B 18/082* (2013.01); *A61F 9/00736* (2013.01);
(Continued)

(58) Field of Classification Search
CPC .................. A61B 18/082; A61B 2018/00214; A61B 2018/00601; A61B 2018/00672; A61B 2018/00702; A61B 2018/00761; A61F 2009/00887; A61F 2009/00889; A61F 9/00736; A61F 9/00754
See application file for complete search history.

(56) References Cited

U.S. PATENT DOCUMENTS 4,227,535 A   10/1980   Connor
4,301,802 A   11/1981   Poler
(Continued)

FOREIGN PATENT DOCUMENTS

JP    2008-155038    7/2008
WO    WO 99/60936    12/1999
(Continued)

OTHER PUBLICATIONS

European Patent Office, Supplementary European Search Report and Opinion, European Patent Application No. EP 13177659.3, Feb. 28, 2014, six pages.

(Continued)

*Primary Examiner* — Michael Peffley
*Assistant Examiner* — Daniel Fowler
(74) *Attorney, Agent, or Firm* — Fenwick & West LLP

(57) ABSTRACT

A surgical device and procedure are provided for performing microsurgery, including a capsulotomy of a lens capsule of an eye. The device has an elastically deformable cutting element mounted within an elastomeric suction cup. The suction cup is attached to an arm for manipulating the device. The device can be inserted into the anterior chamber of the eye, through a corneal incision, to cut a piece from the anterior portion of the lens capsule of the eye. The device is secured against the lens capsule using suction applied by one or more suction elements. The device is then removed from the eye, with the cut piece of membrane retained within the device by suction.

30 Claims, 17 Drawing Sheets

Related U.S. Application Data

No. 12/990,163, filed as application No. PCT/US2009/043828 on May 13, 2009, now Pat. No. 8,702,698.

(60) Provisional application No. 61/127,700, filed on May 15, 2008, provisional application No. 61/201,465, filed on Dec. 11, 2008.

(51) Int. Cl.
  *A61B 18/08* (2006.01)
  *A61F 9/008* (2006.01)
  *A61B 18/00* (2006.01)

(52) U.S. Cl.
  CPC .......... *A61B2018/00214* (2013.01); *A61B 2018/00601* (2013.01); *A61B 2018/00672* (2013.01); *A61B 2018/00702* (2013.01); *A61B 2018/00761* (2013.01); *A61F 2009/00887* (2013.01); *A61F 2009/00889* (2013.01)

(56) References Cited

U.S. PATENT DOCUMENTS

| | | | |
|---|---|---|---|
| 4,570,632 A | 2/1986 | Woods | |
| 5,064,994 A | 11/1991 | Urban | |
| 5,269,787 A | 12/1993 | Cozean, Jr. et al. | |
| 5,345,935 A | 9/1994 | Hirsch et al. | |
| 5,346,491 A | 9/1994 | Oertli | |
| 5,423,330 A | 6/1995 | Lee | |
| 5,423,841 A | 6/1995 | Kornefeld | |
| 5,470,352 A | 11/1995 | Rappaport | |
| 5,569,280 A | 10/1996 | Kamerling | |
| 5,624,392 A | 4/1997 | Saab | |
| 5,669,923 A | 9/1997 | Gordon | |
| 5,860,994 A | 1/1999 | Yaacobi | |
| 5,873,883 A | 2/1999 | Cozean, Jr. et al. | |
| 5,972,011 A | 10/1999 | Pierce et al. | |
| 6,066,138 A | 5/2000 | Sheffer et al. | |
| 6,165,190 A | 12/2000 | Nguyen | |
| 6,306,155 B1 | 10/2001 | Chandler et al. | |
| 6,551,326 B1 | 4/2003 | Van Heugten et al. | |
| 6,629,980 B1 | 10/2003 | Eibschitz-Tsimhoni | |
| 6,758,857 B2 | 7/2004 | Cioanta et al. | |
| 6,887,261 B1 | 5/2005 | Peyman | |
| 7,011,666 B2 | 3/2006 | Feinsod | |
| 8,137,344 B2 | 3/2012 | Jia et al. | |
| 8,162,931 B2 | 4/2012 | Ben-Nun | |
| 8,235,978 B2 | 8/2012 | Ben-Nun | |
| 8,657,813 B2 | 2/2014 | Ben-Nun et al. | |
| 2004/0010284 A1 | 1/2004 | Maloof et al. | |
| 2004/0092982 A1 | 5/2004 | Sheffer | |
| 2004/0106929 A1 | 6/2004 | Masket | |
| 2004/0260254 A1 | 12/2004 | Neilson et al. | |
| 2005/0165346 A1 | 7/2005 | Neilson et al. | |
| 2005/0171531 A1 | 8/2005 | Eliachar et al. | |
| 2006/0009782 A1 | 1/2006 | Brown | |
| 2006/0100617 A1 | 5/2006 | Boukhny | |
| 2006/0105309 A1 | 5/2006 | Stoll et al. | |
| 2006/0195076 A1 | 8/2006 | Blumenkranz et al. | |
| 2006/0254912 A1 | 11/2006 | Nussinovitch | |
| 2006/0259053 A1 | 11/2006 | El-Mansoury | |
| 2006/0264990 A1 | 11/2006 | Michelson et al. | |
| 2006/0271030 A1 | 11/2006 | Francis et al. | |
| 2006/0271188 A1 | 11/2006 | Brown | |
| 2007/0049957 A1 | 3/2007 | Benitez et al. | |
| 2007/0173811 A1 | 7/2007 | Couture et al. | |
| 2007/0191862 A1 | 8/2007 | Ellis | |
| 2007/0287999 A1* | 12/2007 | Malecki | A61B 18/1492 606/41 |
| 2008/0015488 A1 | 1/2008 | Tu et al. | |
| 2011/0118734 A1 | 5/2011 | Auld et al. | |
| 2014/0074088 A1 | 3/2014 | Ben Nun et al. | |

FOREIGN PATENT DOCUMENTS

| | | |
|---|---|---|
| WO | WO 01/56519 | 8/2001 |
| WO | WO 02/43632 | 6/2002 |
| WO | WO 03/022191 | 3/2003 |
| WO | WO 2004/017877 | 3/2004 |
| WO | WO 2005/082302 | 9/2005 |
| WO | WO 2007/120775 | 10/2007 |

OTHER PUBLICATIONS

European Patent Office, Supplementary European Search Report and Opinion, European Patent Application No. EP 13177650.2, Feb. 28, 2014, six pages.

European Patent Office, Supplementary European Search Report, European Patent Application No. EP 09747497.7, Mar. 12, 2012, five pages.

European Patent Office, Supplementary European Search Report, European Patent Application No. EP 09747497.7, Jun. 17, 2011, eight pages.

PCT International Search Report and Written Opinion, PCT Application No. PCT/US2009/043828, Jul. 9, 2009, fifteen pages.

State Intellectual Property Office of the People's Republic of China, First Office Action, Chinese Patent Application No. 201310558068.7, Jan. 20, 2015, nineteen pages.

State Intellectual Property Office of the People's Republic of China, First Office Action, Chinese Patent Application No. 200980117511.9, Aug. 22, 2012, fifteen pages.

State Intellectual Property Office of the People's Republic of China, Second Office Action, Chinese Patent Application No. 200980117511.9, Apr. 12, 2013, eight pages.

United States Office Action, U.S. Appl. No. 14/106,603, Sep. 2, 2015, fifteen pages.

United States Office Action, U.S. Appl. No. 14/106,603, Sep. 16, 2014, eleven pages.

United States Office Action, U.S. Appl. No. 14/106,603, Feb. 24, 2014, eight pages.

United States Office Action, U.S. Appl. No. 12/990,163, Oct. 31, 2013, twelve pages.

* cited by examiner

OPHTHALMIC SURGICAL DEVICE FOR CAPSULOTOMY

CROSS-REFERENCE TO RELATED APPLICATIONS

This application is a continuation of U.S. patent application Ser. No. 14/106,603, filed on Dec. 13, 2013, which is a continuation of U.S. patent application Ser. No. 12/990,163, filed on Dec. 10, 2010 (now issued as U.S. Pat. No. 8,702,698, issued Apr. 22, 2014), which is a national phase entry of PCT/US09/43828, filed on May 13, 2009, which claims the benefit of U.S. Provisional Application No. 61/127,700, filed May 15, 2008, entitled "Ophthalmic Surgical Device for Capsulotomy," and of U.S. Provisional Application No. 61/201,465, filed Dec. 11, 2008, entitled "Ophthalmic Surgical Device for Capsulotomy," the entire disclosures of which are hereby incorporated by reference herein, including any appendices or attachments thereof, in their entirety for all purposes.

BACKGROUND

This invention pertains in general to microsurgery of tissue, and more specifically to procedures and devices for creating precise openings in tissue of a desired diameter and shape. For example, the procedures and devices can be used in ophthalmic surgery of the anterior lens capsule membrane of an eye.

Lens cataract is the leading cause of blindness worldwide and surgical treatment by cataract removal is the treatment of choice. A cataract is a clouding that develops in the lens of the eye or in its envelope. The creation of areas of opacity in the lens obstructs the passage of light. The lens of the eye is supposed to be transparent. If the lens develops opaque areas, as in a cataract, the lens must be surgically removed. If no lens is present in the eye, heavy corrective glasses are required to focus an image on the retina. The lens, however, can be replaced with an artificial interocular lens (IOL) to provide better vision after cataract removal.

The removal of the lens for replacement with an IOL is a surgical procedure that requires substantial precision. The lens is completely enclosed by a membrane called the lens capsule, so the surgeon must first cut through the capsule to access the lens. It is important to cut the capsule in just the right way. If the lens capsule has been cut correctly, and not damaged during the cataract removal, then it can be used to hold an IOL. The implantation of an IOL requires the creation of an opening in the lens capsule that is precisely centered, sized, and shaped for implant stability and for optimal IOL function. The matching of the lens capsule opening size to the peripheral margins of the IOL is critical. The goal of the surgeon is to create a perfectly circular (e.g., 5.5+/−0.1 mm diameter) hole in the capsule, centered exactly on the optical axis of the eye, with no tears or defects in the edge of the hole. Tears or defects on the edge of the hole make the capsule very weak and vulnerable to losing the ability to hold the IOL properly. Different IOL designs may require a different diameter for the hole (e.g., ranging from 4.5+/−0.1 mm to 5.75+/−0.1 mm), but whatever the prescribed diameter is, the accuracy of the surgeon in actually achieving it is very important for proper outcome of the cataract surgery.

Creating an opening in the lens capsule with this required level of precision is a difficult task for a surgeon controlling and guiding conventional hand-held cutting instruments and attempting to trace a precise circular route on the lens capsule. The present state of the art for performing a capsulotomy (the creation of an opening in the lens capsule) is for the surgeon to manually create a small tear in the anterior region of the lens capsule. With great caution, the surgeon then uses a small needle-like cystotome and/or tweezers to try to extend the edge of the tear so as to follow a circular path of the specified diameter and centered on the optic axis of the eye. In practice it often happens that the hole does not end up circular, or the correct diameter, or centered on the optic axis. There can also be radial tears in the edge of the hole that greatly weaken the capsule. As a result of any of these errors, the capsule may not be able to hold the IOL properly.

A number of devices have attempted to address the capsulotomy problem, but these devices still raise a number of challenging problems. Electrocautery devices have been used in the past to try to burn the lens capsule tissue and/or weaken it enough so that it is possible to then go in with hand-held tweezers and more easily tear out the circular patch of membrane. However, these devices often require massive heating elements to heat up the tissue, and so are rather bulky devices for use in performing delicate capsulotomy procedures on small tissue structures. Further, applying heat to a patient's eye to burn tissue is generally a risky procedure. The heat is often applied for a long time, lengthening the procedure and putting the patient at risk. With these electrocautery instruments, it is necessary to put a great deal of energy into the eye, thereby risking damage to tissue near to the capsule. In addition, the electrocautery devices do not complete the capsulotomy, but instead inconveniently leave the partially burnt or weakened capsule behind, thus requiring yet another step and another tool (e.g., tweezers) to fish out the capsule piece for removal. This adds further time to the procedure and puts the patient at risk by requiring more than one tool to be placed in proximity to the patient's eye.

Mechanical knife devices have also been used for performing capsulotomies. These devices are used to try to cut the capsule membrane with a small knife, applying the same cutting mechanism as would be used with a large handheld knife. The problem with cutting tissue on the microscale level with a knife is that the volume of tissue is so small, it has microscopic stiffness. Therefore, the tissue must be stretched relatively far to build up enough stress to provide the force against the cutting edge of the knife (no matter how sharp) for cutting to occur. The scale of stretching is up to a millimeter, and this distortion is greater than the desired precision (e.g., less than 0.1 mm), so it is not a satisfactory mechanism. Also, in practice, several passes with the knife may have to be made over the same cutting location to actually cut all the way through the membrane. Further, precise microcuts are often not easily reproducible with these microknives.

Given the drawbacks of existing treatment devices/procedures for lens capsule surgery, improved techniques and devices for performing microsurgery are needed.

SUMMARY

Embodiments of the invention provide microsurgery techniques and devices for performing, for example, lens capsule surgery. Embodiments of the invention automate the capsulotomy step of lens capsule surgery, such as for a cataract operation, while the other steps of the cataract operation are not impacted and so can be performed in the usual manner. In various embodiments, an opening is created in the lens capsule of the eye using a device that includes a cutting instrument and a mechanism for creating the cut along a desired cutting path (e.g., a circle). In some embodiments, the surgeon centers the device over the lens, presses a button, and within 10 seconds or less the device can be removed from the eye along with the circular patch of capsular membrane that it has cut out. The microsurgical device removes many of the manual steps performed by surgeons in previous techniques, which in turn facilitates more precise cutting of the lens capsule. This allows for surgical procedures that are relatively short in duration compared to previous surgical procedures, and it allows those procedures to be accomplished reliably with average surgical skill. The microsurgical device also addresses many of the problems described above with automated devices, including issues with bulky devices, lengthy procedures, risky burning of tissue, lengthy time periods for application of heat, multistep procedures involving multiple tools, microscopic stiffness problems with cutting tissue, among others.

Embodiments of the invention include devices and methods for performing a capsulotomy. In one embodiment, the device includes a suction cup having a roof and an underside, the underside having inner and outer chambers, an arm attached to the suction cup for moving the device into contact with the lens capsule, and one or more suction elements connected to the suction cup. The elements can provide suction to the chambers to secure the suction cup to the lens capsule of the eye. The elements can also be configured for providing suction (e.g., to the inner chamber) to retain the severed portion during removal of the device. A cutting element mounted to or mounted in relation to the suction cup (e.g., mounted to the underside of the suction cup or otherwise mounted to that the cutting element is positioned to face the tissue) is configured to cut a portion of tissue (e.g., a circular portion) of the lens capsule pulled into the suction cup by the suction provided by the suction elements.

In operation, the surgeon moves a capsulotomy device (e.g., the device described above) to a position proximate to the lens capsule of the eye. Suction can be applied to the suction cup for securing the cup to the lens capsule (e.g., by pulling tissue into the suction cup), and for pulling tissue of the lens capsule into the suction cup against a cutting element mounted to the suction cup. The procedure further includes cutting a portion of the tissue (e.g., a circular portion) of the lens capsule pulled into the suction cup. The suction can then be reduced for releasing the suction cup from the tissue, and the device removed from the eye.

In another embodiment of the method involving a capsulotomy device (e.g., the device described above), the device is again moved into contact with the lens capsule, and suction is applied to the suction cup to secure the suction cup against the lens capsule. A circular portion of the tissue of the lens capsule is cut with the cutting element. Suction is then reduced (e.g., to the inner chamber) for releasing the suction cup and retaining the circular portion severed in the suction cup. The device is then removed from the eye and the portion of tissue severed retained by suction within the suction cup (e.g., the inner chamber).

In other embodiments of the invention for performing microsurgery of tissue (e.g., including tissue other than the lens capsule), the device again includes a suction cup with inner and outer chambers, an arm attached to the suction cup for moving the device into contact with the tissue, and one or more suction elements connected to the suction cup. The elements can provide suction to the chambers to secure the suction cup against the tissue. A cutting element is located within the outer chamber and mounted to the suction cup (e.g., around the periphery of or within an annular region of the suction cup). The cutting element is configured to cut free a portion of the tissue pulled by suction into the suction cup. The suction elements can release the suction to release the suction cup from the tissue while providing suction to the inner chamber for retaining the severed tissue portion during removal of the device.

In operation, the surgeon moves a microsurgery device (e.g., the microsurgery device above) to a position proximate to the tissue, and applies suction to the suction cup for pulling an area of the tissue into the suction cup to secure the suction cup against the tissue. The suction also pulls the tissue into position for cutting. The method further includes cutting free a portion of the tissue pulled into the suction cup against a cutting element. The suction is then released from one of the chambers (e.g., the outer chamber) of the suction cup to release the cup from the tissue. The suction is however maintained in another of the chambers (e.g., the inner chamber) for holding the portion severed in the suction cup. The surgeon removes the microsurgery device from the tissue, along with the portion of the tissue severed, which is retained in the device.

These techniques enable a surgeon to perform minimally invasive microsurgery on tissue, such as the lens capsule, which results in relatively low collateral damage to neighboring tissues as compared with previous treatment techniques. The techniques described herein also provide a high level of control of the positioning and orientation of the cutting instrument for precise location and sizing of the incision in the lens capsule.

The figures depict an embodiment of the present invention for purposes of illustration only. One skilled in the art will readily recognize from the following description that alternative embodiments of the structures and methods illustrated herein may be employed without departing from the principles of the invention described herein.

DETAILED DESCRIPTION

Microsurgery/Capsulotomy Device

Embodiments of the invention are described herein in the context of a lens capsule surgery in which a portion of the anterior surface of a lens capsule is cut. This technique may be used for performing a treatment for cataracts in which all or a portion of a lens located within the lens capsule is removed from the eye. The procedure may also be used to create an access hole in the lens capsule through which to implant an artificial lens (e.g., an intraocular lens, or IOL) within the lens capsule. Moreover, the techniques and devices described herein may be useful tools for performing other medical procedures (such as corneal surgeries or surgeries involving tissue other than that in the eye), which may or may not currently exist.

Figure 1:
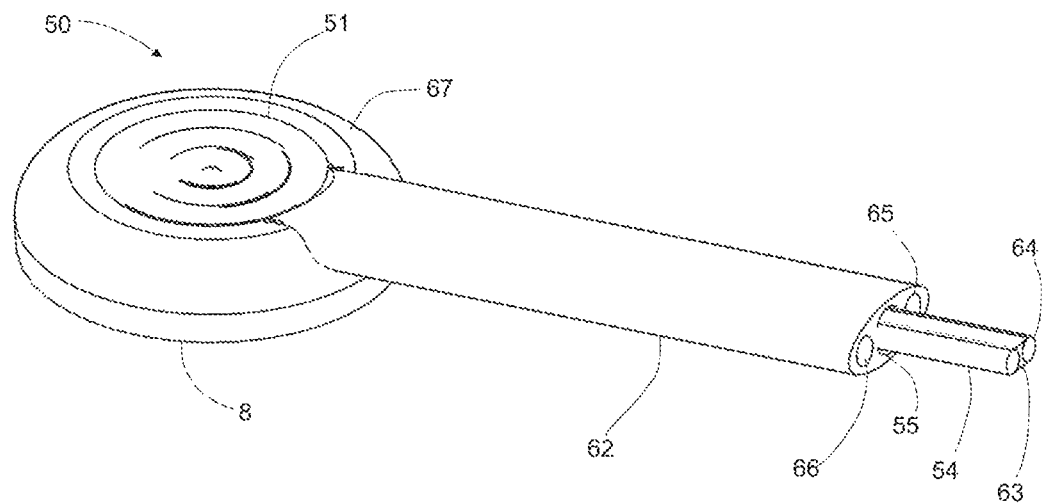
FIG. 1 is a diagram of the microsurgery/capsulotomy device, according to an embodiment of the invention.
Figure 2:
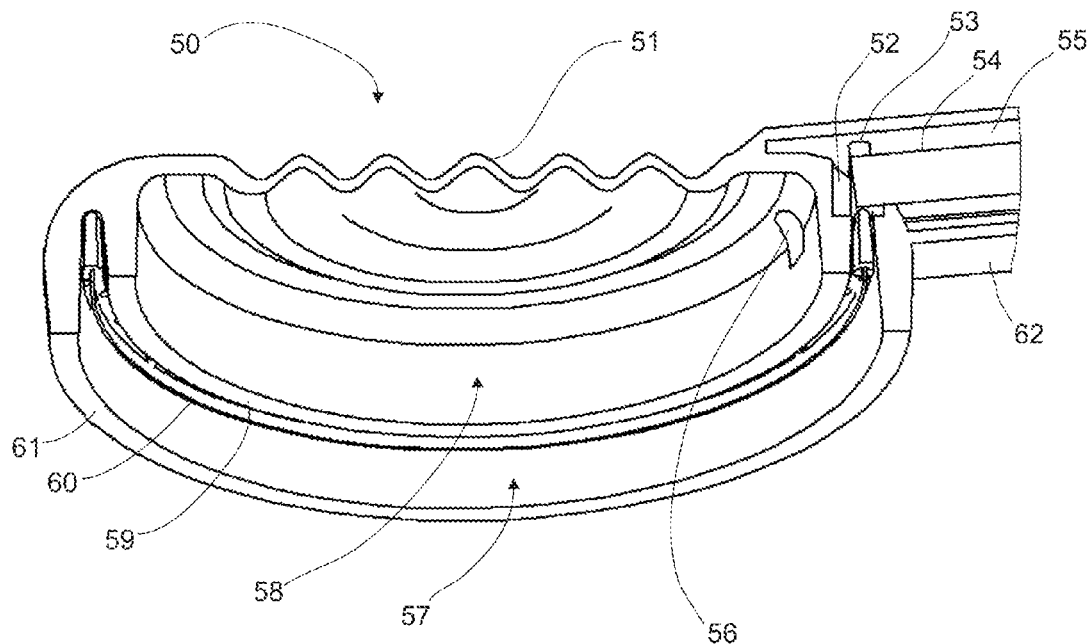
FIG. 2 is a cross-sectional view of the microsurgery/capsulotomy device, according to an embodiment of the invention.

FIG. 1 is a top perspective view of the microsurgery or capsulotomy device, and FIG. 2 is a cross-sectional view of the device, according to an embodiment of the invention. The Figures illustrate that the device (50) has a suction cup (67) and an arm or stem (62). The suction cup (67) has a roof (51) and an underside (8). The underside includes an inner chamber (58) and outer chamber (57). The arm/stem (62) is attached to the suction cup for moving the device into contact with tissue (e.g., the lens capsule). The roof (51) of the inner chamber (58) can be corrugated in some embodiments, such as is shown in FIG. 1, to make it more stretchable to deform as needed to enter the insertion tube (illustrated as item number 4 in FIGS. 3a and 3b).

In some embodiments of the device (50), the suction cup (67) is collapsible to a small cross section so that it can be inserted through a corneal incision (e.g., an incision of less than 3.0 mm in length). After insertion into the anterior chamber of the eye, the suction cup (67) is designed to rapidly return to its circular shape. The suction cup (67) can be made of an elastomeric material such as silicone or polyurethane (e.g., made by casting or by injection molding), though other materials can be used as well. The thinner the walls are, the stiffer (higher durometer) the material can be. The size range for the suction cup would commonly range from about 4.5 mm to about 7 mm in diameter, while the height would commonly range from about 0.5 mm to about 1.5 mm. However, other suction cup sizes and designs are possible. Particularly for surgery performed outside of the eye (e.g., on other parts of the body), the suction cup and overall device size ranges can vary to match the surgical procedure being conducted. After insertion into the anterior chamber of the eye, the device is designed to rapidly return to its circular shape.

There are two types of suction cups (67) that are commonly used with the device (50): solid and inflatable. The solid construction is simpler to make, but the inflatable construction allows passage through a smaller incision, and also develops an internal pressure that can restore the circular shape of the suction cup and cutting element more rapidly. A highly viscous material is typically injected into the eye during surgery to keep the anterior chamber from collapsing due to leakage through the corneal incision, so the suction cup (67) should be designed to move through this material as it recovers its prior shape. After the capsule is cut, the suction cup (67) can be collapsed again to a smaller cross section for removal through the corneal incision. In some embodiments, even though the suction cup (67) is collapsible, it has enough stiffness to be maneuvered to the surgery site, unlike many other devices that require a rod or other element for maneuvering the device into position. For example, the inflatable designs are made relatively stiff by internal pressure. The solid wall of the non-inflatable designs is stiff enough by virtue of having a thicker wall cross section and/or using a higher durometer (stiffer) elastomeric material.

The cutting element (60), which is visible in the cross-sectional view of FIG. 2, is mounted to the suction cup (67). In this embodiment, the cutting element (60) is mounted to the underside of the suction cup (67) within the outer chamber (57), between walls (61) and (59) of the outer chamber (57). However, it can be mounted elsewhere in or on the suction cup (67), or mounted in relation to the suction cup (67) so that the cutting element (60) is positioned to face the tissue to be cut. The cutting element (60) is configured to cut a portion of tissue (e.g., of the lens capsule). In the embodiments of FIGS. 1 and 2, the cutting element (60) is a circular cutting element mounted around the periphery of the underside (8) of the suction cup (67). However, the cutting element (60) can take other shapes (e.g., elliptical, square, rectangular, irregular, and other shapes) for different types of surgical procedures where a differently-shaped incision in the tissue is desired. Similarly, the suction cup (67) can take on other shapes, as well. The cutting element of the FIG. 2 embodiment is a circular ring having a diameter that produces a desired hole or opening in the tissue.

There are at least three different types of cutting elements (50) that can be used with the embodiments of device (50): electrical, mechanical, and combined electro-mechanical, though other designs could be used, as well. The electrical cutting element functions as a resistor. A very short electrical pulse quickly heats up the element (e.g., to greater than 500°

C., such as 600° C., 700° C., 800° C., 900° C., 1000° C., 1200° C., 1500° C., and so forth). In some embodiments, the heating process lasts for a few microseconds (e.g., 10 microseconds or less), though heating times can differ in other embodiments (e.g., 1 microsecond, 5 microseconds, 10 microseconds, 20 microseconds, 1 millisecond, 5 milliseconds, etc.). The duration of the electrical discharge is too short for heat to travel more than a few microns by conduction from the cutting element (60), so for a few microseconds the thin layer of water that is trapped between the capsule and the cutting element (60) absorbs the energy of the discharge and forms steam. The steam expands and increases the tensile stress in the capsule enough to tear it.

Since the electrical current is applied for only a few microseconds, tissue is not burned as it is with electrocautery instruments used in the past for performing capsulotomies. Due to this, the device (50) avoids the risks associated with burning tissue in a patient's eye, with possible collateral damage to nearby tissue, with lengthy application of heat, and other problems. The energy of the electrical cutting element of device (50) is instead used to make a micro steam explosion to tear the capsule, not burn it. In addition, the electrical cutting element of device (50) completes the severing of the tissue to free the severed piece from the capsule, unlike electrocautery devices that often only weaken the tissue and require tweezers to remove the severed piece. Further, in some embodiments, the electrical cutting element has a mass of 0.35 milligrams or less, so bulky heating elements are not required as are commonly found with electrocautery instruments.

With the mechanical cutting element, the element has one or more ultrasharp microteeth (or other tissue-severing mechanism) that pierce the capsule as the force of suction pulls the membrane past the teeth (described below) to sever the circular patch. As explained above, mechanical knife devices used in the past for performing capsulotomies use the knife to stretch the tissue to provide enough force against the cutting edge. In contrast, in the present invention, the reaction force needed for cutting with the mechanical cutting element of device (50) comes from suction supplied by the device, not from trying to use the stiffness of the tissue by pushing against it. The suction pulls the tissue perpendicularly into the cutting edge, so there is no lateral distortion away from where the cut is supposed to go, and precision microcuts can be reproducibly made. In addition, a complete cut can be made with the cutting element (60), as opposed to the multiple passes that are frequently required with microknives used in the past. Though the cutting element is a continuous ring in the embodiments of FIGS. 1 and 2, this is not required. It could instead be a non-continuous ring, or could include discrete microteeth anchored in an elastomeric support ring.

The combined electro-mechanical cutting element has 1 microtooth (or optionally, more than one) or other tissue severing mechanism that produces an initial tear in the capsule. The tear is propagated using the electrical cutting element design for applying a short electrical pulse, as explained above. The tear can be propagated to complete the capsulotomy by a lower steam pressure than would be required for an intact capsule.

The stem (62) that extends from the suction cup (67) contains lumens (55, 65, 66) to transport liquids and gases. In some embodiments of the device, one or more of the lumens contain electrical conductors, such as the electrical leads (54, 64) shown in FIG. 1. In the embodiment shown, the lumen (65) connects to the inner chamber (58) of the suction cup via orifice (56). The central lumen (55) connects to the outer chamber (57) of the suction cup through orifice (52). For devices using electrical cutting elements, the electrical leads (54, 64) can be separated by an insulator (63) located in lumen (55). The leads (54, 64) do not fill the lumen (55), but instead leave some free space for fluids to pass through too. The electrical lead end (53), as it connects to the cutting element (60) in the outer chamber (57), is illustrated in FIG. 2. Lumen (66) is used for inflating and deflating the suction cup (67), which is relevant for embodiments in which the suction cup is inflatable (described in more detail with regard to later Figures).

One or more of the lumens (55, 65, 66) can also act as suction elements that connect to and provide suction to the suction cup (67). In one embodiment, suction can be applied independently to the inner chamber (58) and to the outer chamber (57). For example, lumen (55) connecting the outer chamber (57) can provide suction to that chamber, while lumen (65) connecting to the inner chamber 58 can provide suction to that chamber. The functions of the different lumens (55, 65, 66) can differ across different embodiments of the device (50).

The suction applied to the suction cup (67) can serve a number of purposes. The suction can be used to secure the device (50) to the tissue for the cutting procedure. The suction can also provide a vacuum seal against the tissue. The suction can further pull portions of the tissue up into the suction cup (67) for securing the suction cup (67) against the tissue or for permitting severing of the tissue using the cutting element, as explained in more detail regarding FIGS. 4-9. The applied suction force can stretch the capsular membrane over the edge of the cutting element (60) to create a state of high tensile stress exactly on the circle where cutting is desired. Suction can also be used to retain the cut portion of tissue inside the device (50) during removal. In one embodiment, suction is provided to the outer chamber (57) to create a seal against the tissue and to apply tension to the annular region of the lens capsule where a precise cut is to be made, and suction is applied independently to the inner chamber (58) to hold the circular patch of tissue that is to be removed. Since the cutting element (60) is built-in directly to the device (50) that also provides the suction and fluid flushing capabilities, the device (50) can be used in a one-step procedure for performing a capsulotomy, rather than requiring a second step/device for flushing. In the embodiment illustrated in FIGS. 1 and 2, the lumens (55, 65, 66) each run along inside the length of the stem (62). However, other configurations are also possible. For example, the suction cup (67) could be connected to one or more tubes or other elements separate from the stem (62) that provide the same functions as lumens (55, 65, 66).

Figure 3A:
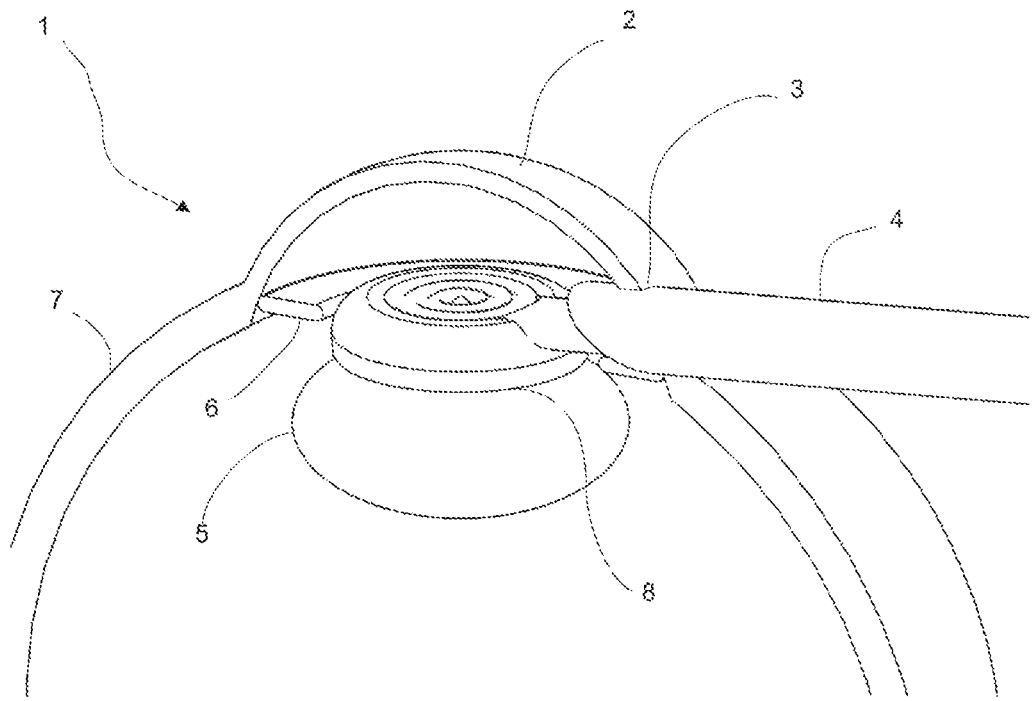
FIG. 3*a* illustrates the microsurgery/capsulotomy device in use in the anterior chamber of the eye, according to an embodiment of the invention.

FIG. 3a shows the device during use in the eye (1), according to an embodiment of the invention. The parts of the eye (1) illustrated in FIG. 3a include the sclera (7), the cornea (2), the iris (6) and the lens capsule (5). In FIG. 3a, the surgeon has made an incision (3) through the cornea (2). In this embodiment, an insertion tube (4) is used to deliver the device (50) to the eye (1) and through the incision (3). However, other delivery mechanisms can be used too. The insertion tube (4) illustrated in FIG. 3a has been pushed through the incision (3) so that the suction cup (67) could be pushed out of the tube (4) and into the anterior chamber of the eye (1).

The device (50) illustrated in FIG. 3a is being used by an ophthalmic surgeon to perform a capsulotomy. That is one of the steps that is typically performed in cataract surgery. The capsule (5) is a transparent membrane that encapsulates the lens of the eye (1). For the operation, the iris (6) is made to stay in its maximum open state to allow the rim of the suction cup (67) to pass through the pupil and make a tight seal between the underside (8) of the cup (67) and the lens capsule (5). A circular hole is cut in the anterior capsule so that the cataractous lens can be removed, and the IOL can be inserted. In some embodiments, the circular opening in the capsule (5) or other tissue is approximately 5.5 mm in diameter. However, other diameter openings can be created with other embodiments, as desired for various surgical procedures (e.g., 1 mm, 5 mm, 10 mm, 20 mm, 100 mm, and so forth). The 5.5 mm diameter circular patch of excised membrane is removed using the device (50) and can be discarded, but the rest of the capsular bag should remain undamaged so that it will have the structural integrity needed to hold the IOL.

Figure 3B:
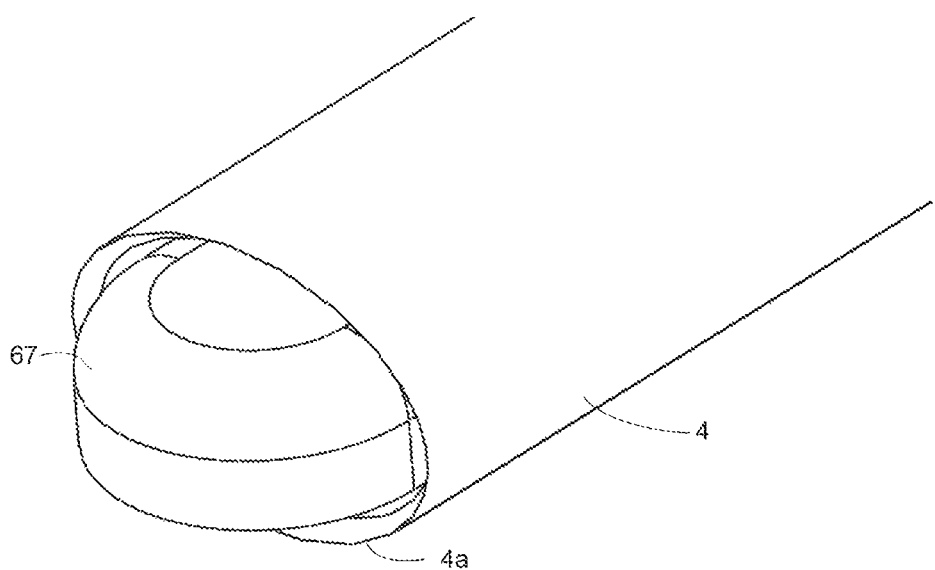
FIG. 3*b* illustrates a suction cup withdrawn into an insertion tube of the device, according to an embodiment of the invention.

FIG. 3b illustrates the deformable device (50) withdrawn inside the insertion tube (4), according to an embodiment of the invention. The device (50) can be pulled into the lumen of the insertion tube (4), and the suction cup (67) can be collapsed to fit inside the tube (4). The cross section of the insertion tube (4) can be elliptical to minimize the vertical stretching of the corneal incision and deformation of the cutting element (60), though it can also be circular or take on other shapes.

Both the suction cup (67) and the cutting element (60) can be made from materials that can restore their circular shape after being pushed out of the insertion tube (4). As stated above, the suction cup (67) can be made from an elastomer (such as the medical grade silicone MED-6015 from NUSIL, INC.®), and the cutting element (67) can be made from a hard elastic material, such as spring steel or stainless steel. Though the cutting element (67) can also be made of other materials and metals. Typically, for electrical cutting elements, the material for the cutting element is electrically conductive, and for mechanical cutting elements, the material is hard enough to pierce the membrane.

For both electrical and mechanical cutting elements, the material is also generally elastic enough to return to its prior shape after being squeezed to get through the corneal incision, or soft enough to be pushed back into circular shape by the polymeric support ring and/or by the suction cup in which it is mounted. For example, for an electrical cutting element, the materials can include those made by photochemical etching, such as spring steel, stainless steel, titanium nickel alloy, graphite, nitinol (NiTi alloy "memory metal"), nickel, nickel-chrome alloy, tungsten, molybdenum, or any other material that will allow the element (60) to return to its prior shape upon exit from the tube (4). Other materials for electrical cutting elements include electrically conductive elastomers, including elastomers (e.g., silicone or polyurethane) mixed with appropriately shaped conductive particles (e.g., silver, gold, graphite, copper, etc) that can establish contact with each other and continue to be in contact with each other for the duration of the electrical discharge. An additional example of a material for electrical cutting elements includes a compliant mesh of very fine wires (e.g., diameter of about 1 or 2 microns) that can be anchored in the elastomeric support ring to make the conductive element. As a further example, materials can be used for electrical cutting elements that are made by sputtering metal onto a polymeric support, such as high conductivity metals (e.g., gold, aluminum, copper, etc.), which can be used to make very thin (e.g., 1 micron) elements with resistance within the usable range (e.g., 1 to 10 ohms) deposited by RF plasma sputtering. As examples of materials used for mechanical cutting elements, they can include photochemically etched metal (e.g., stainless steel), or a relatively hard plastic (e.g., phenolic), among others. Discrete micro teeth could be etched from single crystal silicon. Photochemical etching can used to make cutting elements that have a thickness of, for example, 25 microns, or 12.5 microns, or 5 microns, and so forth.

In embodiments in which the suction cup (67) is inflatable, the cutting element (67) can be helped to return to its ring shape by the inflation of the cup (67). So, in inflatable embodiments, using a material for the cutting element (67) that has ability to return to the ring shape is less important. In embodiments in which the cutting element (60) is an electrical cutting element, the element (60) is composed of a material that is electrically conductive, such as the metals described above.

The insertion tube (4) can be made of various different materials, such as stainless steel or plastic. The insertion tube (4) can be designed to have the lowest possible coefficient of friction, and can also be lubricated to minimize the force needed to slide the suction cup in the tube. The entrance (4a) to the insertion tube is shaped (e.g., beveled) in this embodiment to make it easier to pull the suction cup (67) into the tube (4). The end of the insertion tube is also shaped to facilitate its penetration through the corneal incision. Note in FIG. 3a that the tube of elliptical cross section has been cut at a 45 degree angle (for example) so that the initial entry into the incision is made by just the tip of the tube and with a very small cross section, so the force is low.

Surgical Procedure

Figure 4:
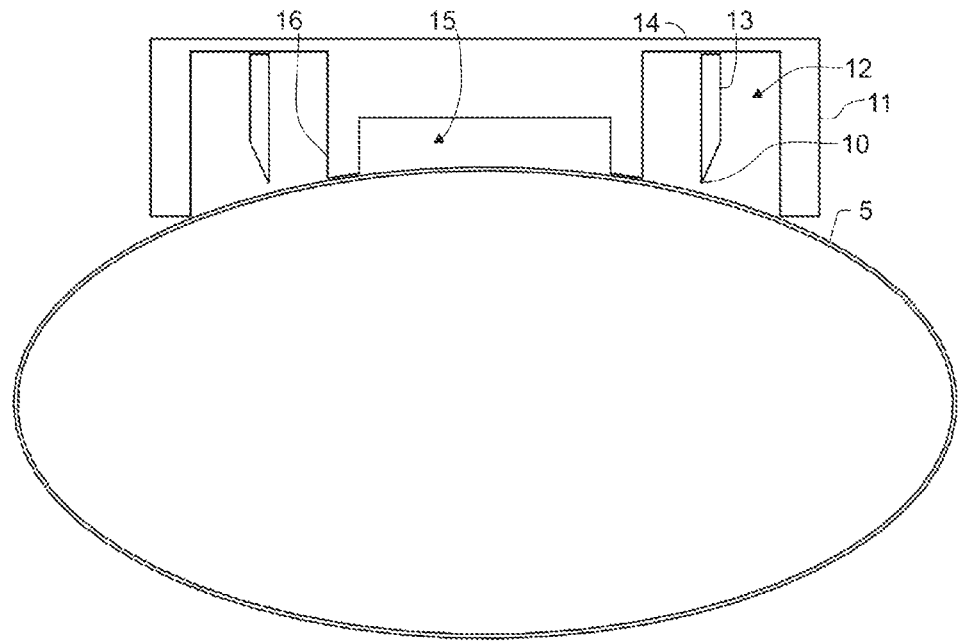
FIGS. 4-9 illustrate schematically the steps involved in the use of the device, according to an embodiment of the invention.

FIGS. 4-9 schematically show the steps in the automated capsulotomy process, according to an embodiment. FIG. 4 illustrates an embodiment of the suction cup (67) in which the cup includes a roof (14) and an outer perimeter (11). In this embodiment, the suction cup (67) includes an outer chamber (12) and an inner chamber (15) separated by a wall (16). Mounted to this embodiment of the suction cup (67) is a cutting element (13) with an edge (10) for cutting tissue. The outer chamber (12) acts as an outer vacuum channel at the circular rim of the suction cup (67) that uses the force of suction to hold the device (50) onto the lens capsule (50), and the device (50) has tubing (described regarding FIGS. 1 and 2) that extends out through the cornea for access to other apparati to provide independent fluid communication to the outer chamber (12) and to the inner chamber (15).

Figure 5:
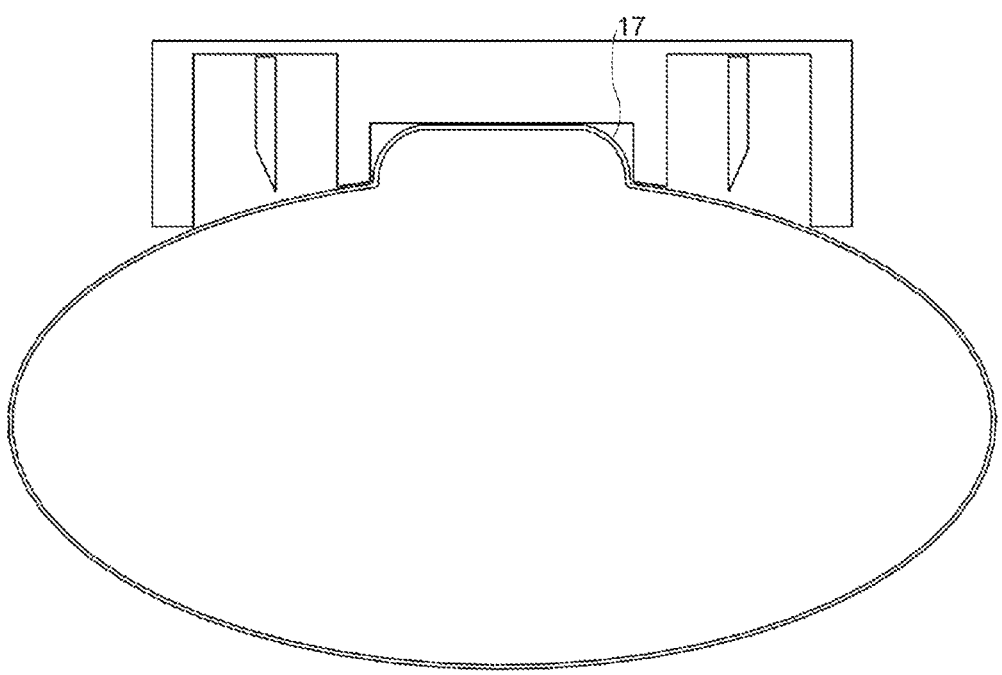

In FIG. 4, the surgeon has brought the suction cup (67) into contact with the capsule (5) centered on the optical axis. The surgeon can then press a button, and the remaining steps that result in a severed tissue patch can occur automatically under computer control. Suction is applied to the inner chamber (15) of the suction cup (67). The suction provided to the inner chamber (15) creates a bulge (17) in the tissue, which is shown in FIG. 5. This bulge locks the capsule (5) in place, and so secures the suction cup (67) against the capsule (5) so it will not slide relative to the capsule (5).

Figure 6:
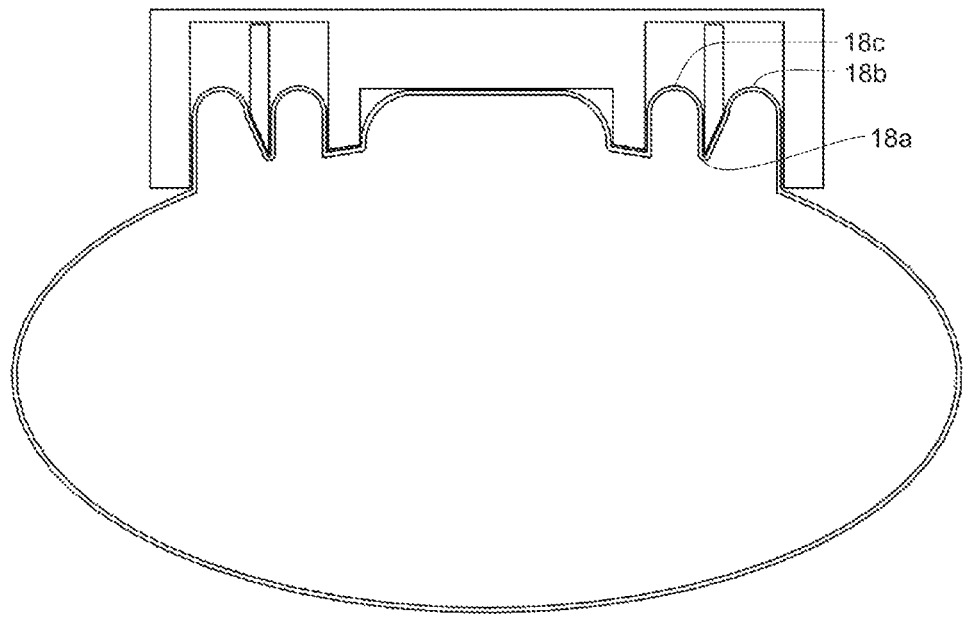

FIG. 6 illustrates the next step in which suction is applied to the outer chamber (12) of the suction cup (67). This produces annular bulges (18b) and (18c) in the capsule (5), stretching it over the edge (10) of the cutting element (13) to produce the maximum tensile stress in the membrane at location (18a), which is the radius at which cutting is desired. The diameter of the final hole might not be equal to the diameter of the cutting element (13) due to the fact that the cutting occurs when the lens is deformed and the capsule (5) is stretched. However, since the process is reproducible, it can be readily determined what diameter hole results from any given diameter of cutting element (13), and adjustments to the cutting element design can be made accordingly.

If the cutting element (13) is a mechanical one, then it can include one or more ultrasharp microteeth that will pierce the capsular membrane. The applied pressure due to the suction pulling the tissue against the cutting element will do the work of moving the cutter completely through the membrane to sever the circular patch. In embodiments in which the cutting element (13) is mechanical, the surgical method skips FIG. 7 and goes directly to FIG. 8.

Figure 7:
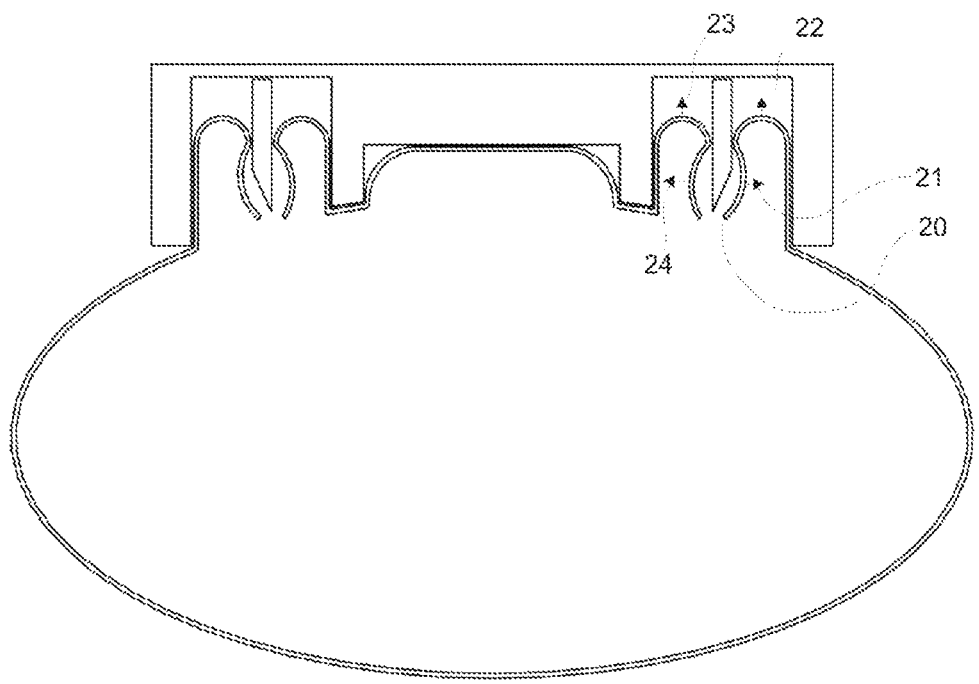

If the cutting element (13) is an electrical one, then it is essentially a heating element (e.g., a resistor). The applied suction pressure will stretch the capsule (5) over the cutting (heating) element (13) to create a circle of high tensile stress, but not enough to tear the membrane. FIG. 7 shows the electrical element (13), and illustrates the instant at which the electrical discharge occurs. The thin film of water trapped between the heating/cutting element (13) and the capsule is heated (e.g., to 1000° C.) in a few microseconds. This becomes high pressure steam that expands and pushes the membrane away from the heating/cutting element (13). The force of suction (22, 23) is already present, acting to stretch the membrane. The additional stretching forces (21, 24) from the expansion of the steam increases the tensile stress enough to create the desired tear (20) in the membrane instantaneously all the way around the circular heating element (13).

Some prior devices require the surgeon to manually hold a cutting element against the capsule, pushing the lens down into the vitreous by a gross displacement until the equal and opposite reaction force can be developed within the fibers of the easily damaged zonules which hold the lens in the eye. Reaction force is also generated in these other devices by increasing the pressure within the vitreous to push back on the lens, but that pressure also pushes on the retina, and is risky. In contrast, with the device (50) described here, the capsule (5) is sucked against the cutting element (13), so the force and reaction force are both right there entirely contained within the device (50) and the capsule (5). The device does not require pushing on other eye structures. Furthermore, uniform, intimate contact over the full 360 degrees of the ring is ensured, unlike with prior, manual push devices, in which the surgeon never knows if he has uniform contact (holding the device with even an imperceptible tilt relative to the lens will cause non-uniform contact force around the ring). With the device (50), since the pressure against the cutting element (13) is uniform, heat transfer will be uniform, and cutting will progress uniformly. In addition, as explained above, the device (50) applies less energy to the tissue for a shorter duration than electrocautery instruments that burn the tissue by applying heat for long durations.

Figure 8:
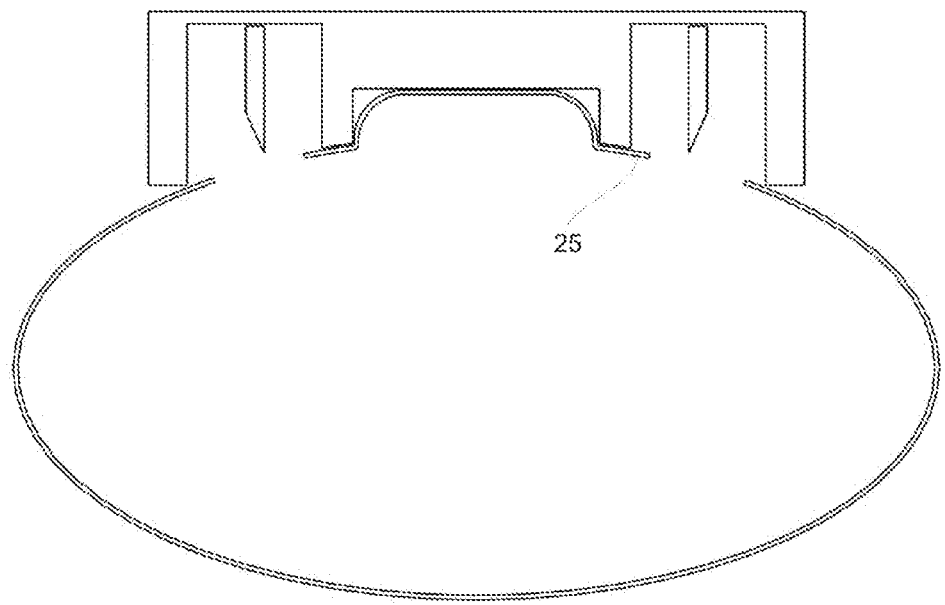
Figure 9:
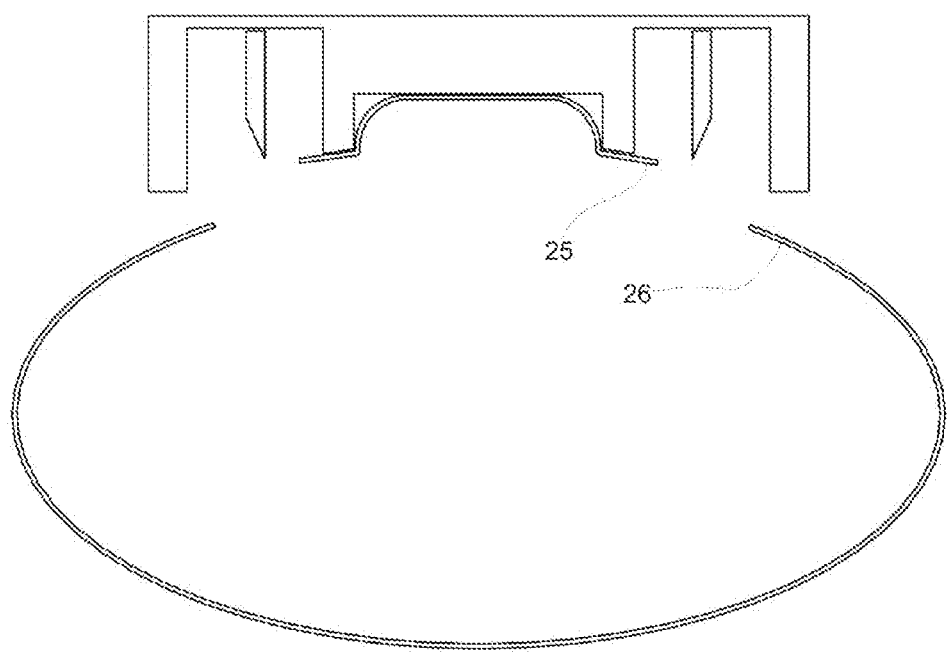

FIG. 8 shows the completely severed circular patch (25), which was severed using any of the types of cutting elements (13) described above. There is no mechanical attachment or adhesion between the capsule (5) and the lens. When the suction to the outer chamber (12) is turned off, fluid can then be injected into the outer chamber (12) as the device (50) is lifted away from the lens. During removal of the device (50) from the location of the surgery, the severed patch of membrane in the inner chamber (15) is carried away in the device since a suction force is maintained there in the inner chamber (15). This leaves the remainder (26) of the capsule (5) behind, as desired.

In summary, as explained above, the suction applied in device (50) can be used to do four things (among others): (a) to provide a clamping force to hold the device to the lens capsule, (b) to stretch the capsule membrane over the cutting element (13) and develop significant tensile stress within the membrane where cutting is desired, (c) to retain the severed patch (35) of membrane within the inner chamber (15) for removal from the eye, and (d) after cutting, to push the device (50) away from the lens by turning off the suction in the outer chamber (12) and injecting liquid (most likely, that which was just sucked into the tube previously) into the outer chamber (12). In addition, the device will function even if there is some leakage, because it is not necessary to isolate fluids as long as the leakage is small enough that the suction flow can maintain the pressure needed to provide the required forces. Thus, the device (50) provides all of these features (e.g., suction, cutting element, etc.) on the scale of the tissue size that the surgeon is attempting to cut. Once the surgeon presses the button, as explained above, the device can typically be removed from the eye (along with the severed piece of tissue) within a few seconds (e.g., 1 second, 2 seconds, 5 seconds, 10 seconds, 20 seconds, 50 seconds, 1 minutes, and so forth).

Cutting Element Designs

Figure 10:
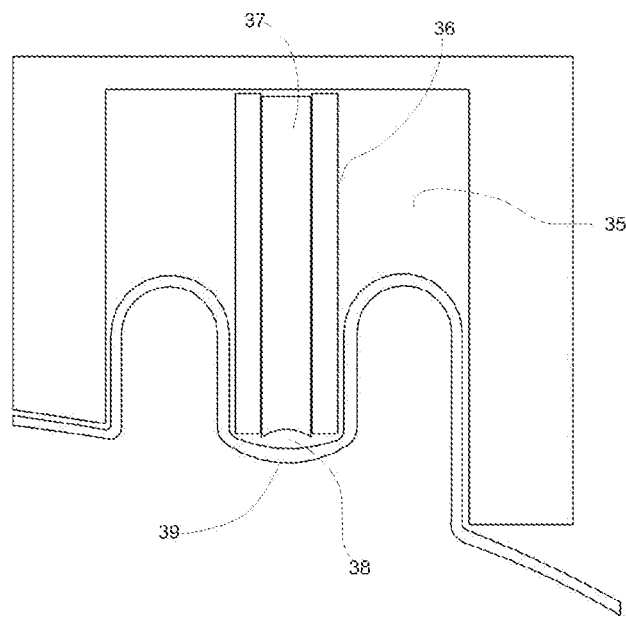
FIGS. 10-11 are cross-sectional views of an overetched heating element with insulated sides in the device, according to an embodiment of the invention.
Figure 11:
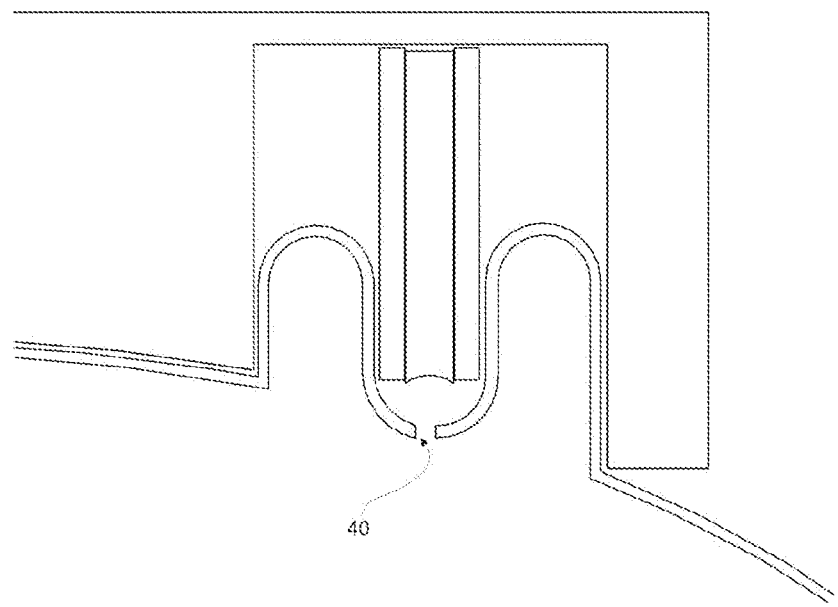

FIGS. 10-11 show a schematic cross section of an electrical cutting element (37), according to an embodiment. In this design, the sides of the element (37) have a nonconducting layer (36) (e.g., plastic or another nonconducting material). With this layer (36), the heat of the element (37) is focused at the edge (38) of the element (37). Thus, the steam will be produced only at the edge (38) to stretch the membrane at the bend (39) of the tissue and create the cut (40), which is shown in FIG. 11.

Figure 12:
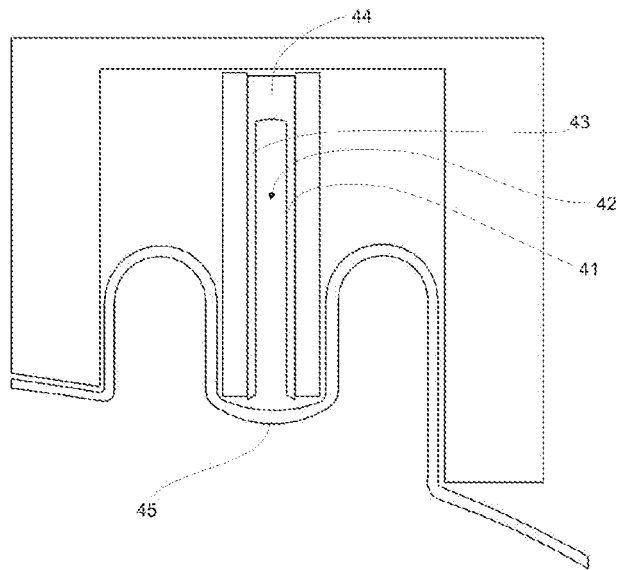
FIG. 12 is a cross-sectional view of a heating element with a deep cavity, according to an embodiment of the invention.

FIG. 12 shows a schematic cross section of an electrical cutting element, according to an embodiment. In this design, the element includes a lumen that is constructed to allow a greater volume of trapped water (42) and a greater surface area of contact between the water and the sides of the element (41, 43, 44). When discharged, this will create a directed jet of steam to cut the membrane at (45).

Figure 13:
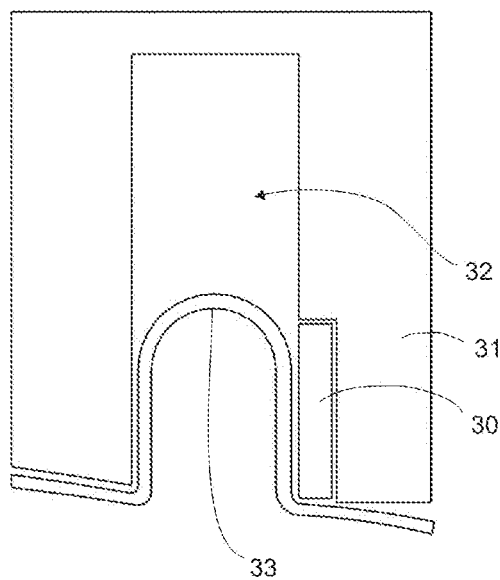
FIG. 13 is an illustration of a side cutting geometry, according to an embodiment of the invention.
Figure 14:
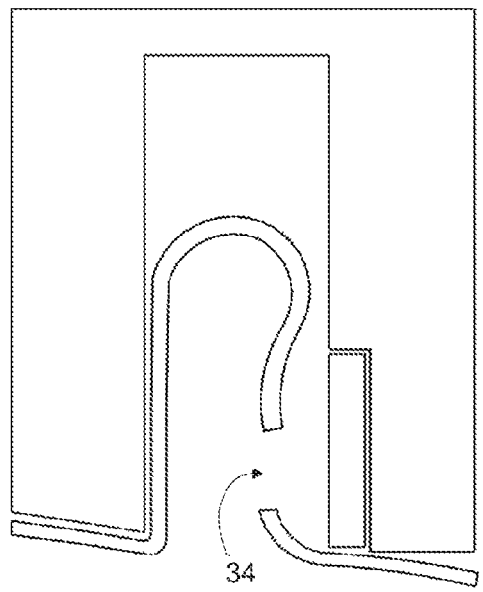
FIG. 14 is an illustration of the device after a side cut has been completed, according to an embodiment of the invention.

FIGS. 13-14 show in schematic cross section of an electrical cutting element (30), according to an embodiment. This element (30) creates a cut (34) in the side of the bulge (33) of tissue, as the element (30) is positioned over to the side of the device (50). Other designs are also possible, in which the cutting element is positioned differently in the suction cup and/or the tissue is cut at other locations.

Other Embodiments of the Microsurgery/Capsulotomy Device

Figure 15:
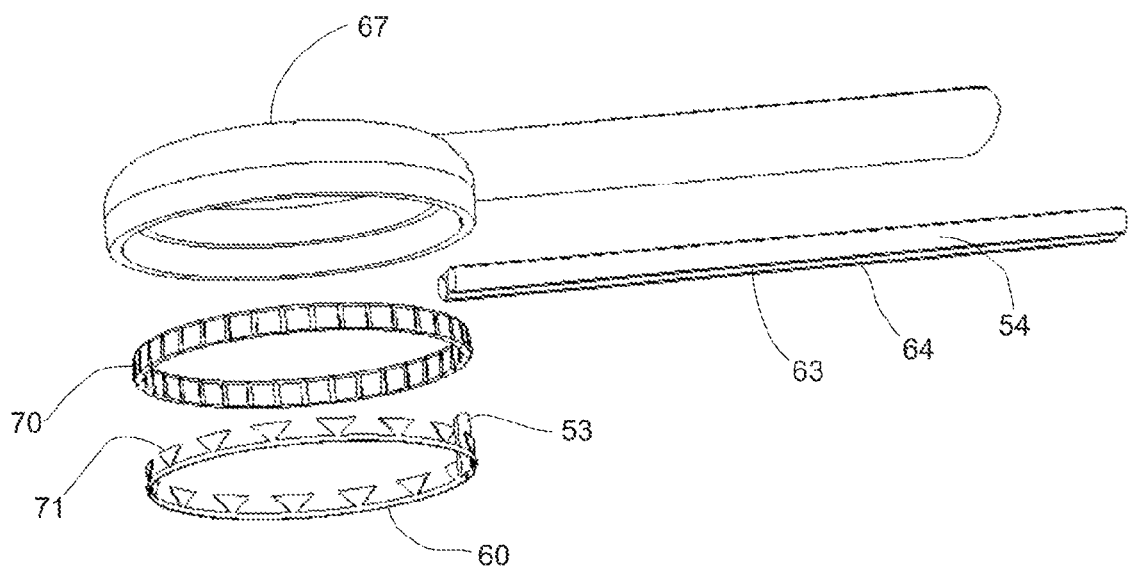
FIG. 15 is an exploded view of the device components, according to an embodiment of the invention.
Figure 16:
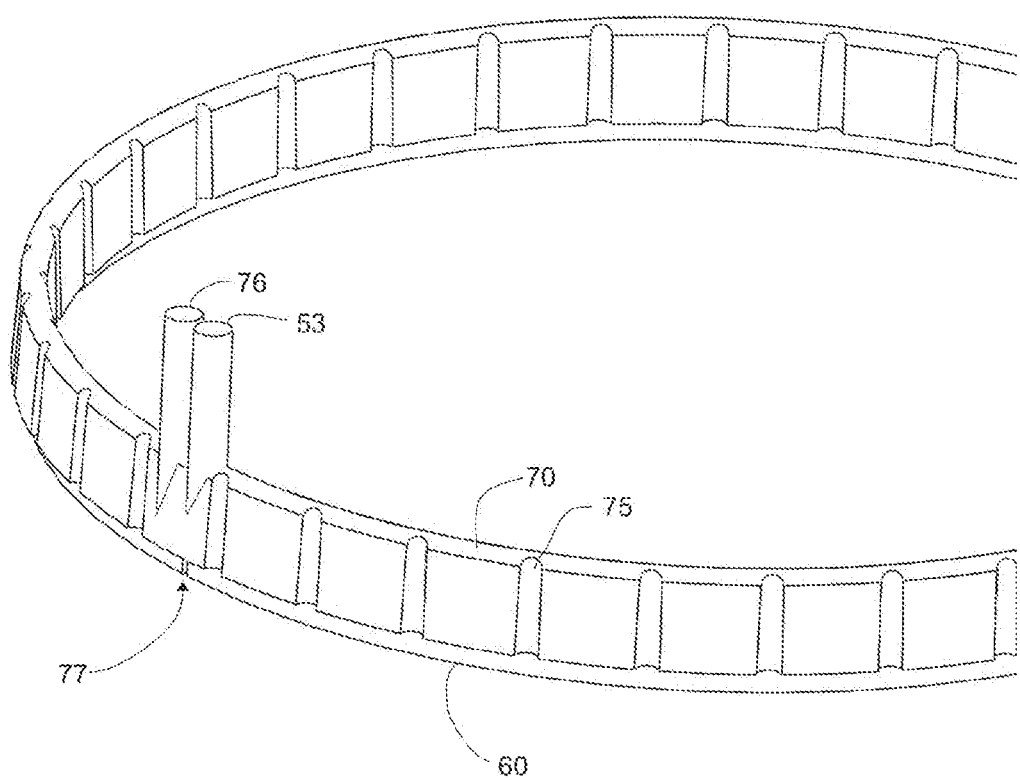
FIG. 16 is a close-up view of a heating element and its support ring, according to an embodiment of the invention.

FIGS. 15-16 show an exploded view of a device, according to an embodiment. The device in this design has a suction cup (67), a cutting element support ring (70), and an electrical cutting element (60) with tabs (71) that anchor it to the support ring (70). Grooves (75) in the sides of the support ring (70) ensure the distribution of suction throughout the outer chamber. Leads (53, 76) connect to the ends of the wires (54, 64) which are separated by insulator (63). There is a small gap (77) so that the electrical current is forced to go all the way around the ring (70). The gap is small enough that the steam bubble produced during discharge is big enough to continue the tear in the membrane past the gap (77).

Figure 17:
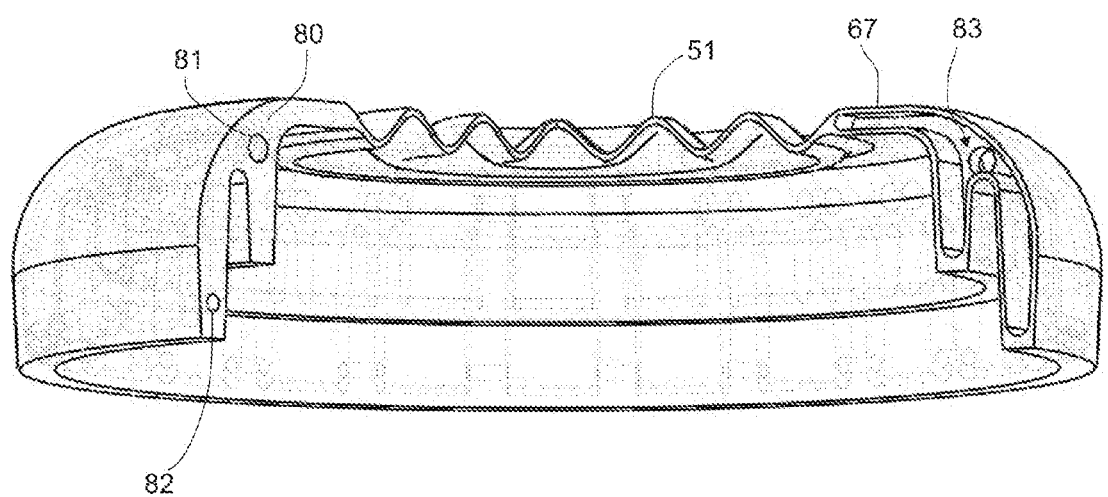
FIG. 17 is an illustration of an inflatable/collapsible suction cup design with the web and skin structure, according to an embodiment of the invention.
Figure 18:
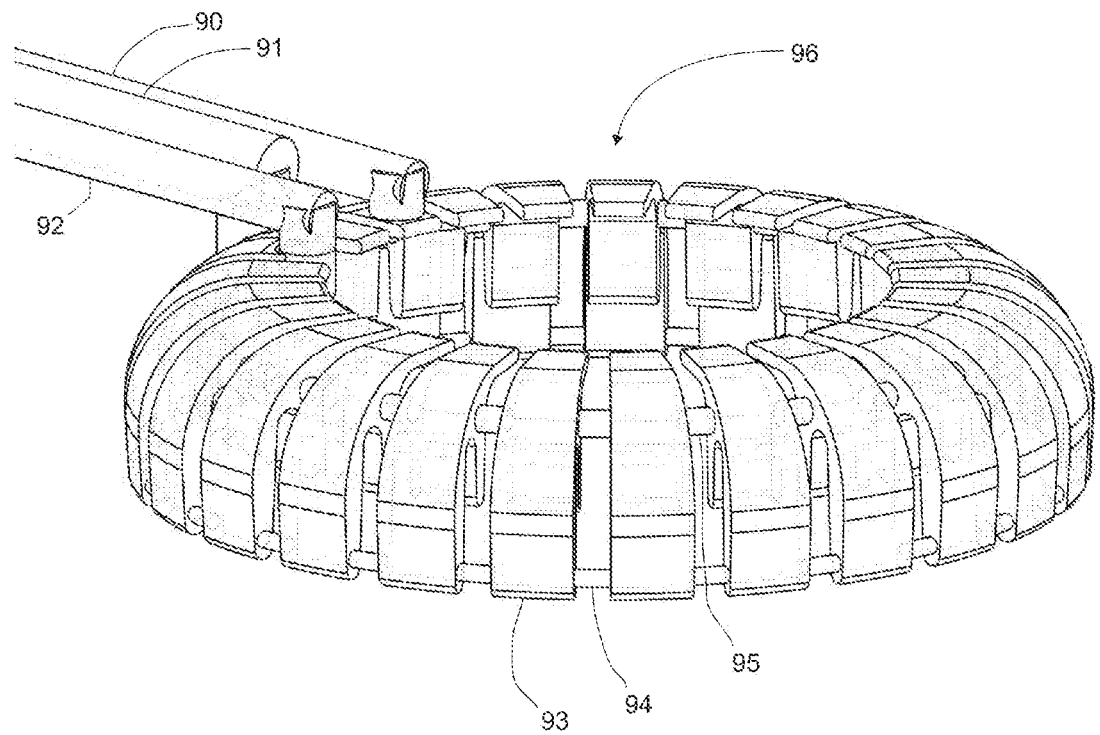
FIG. 18 is an illustration of a meltable wax insert to mold hollow spaces in the web and skin structure, according to an embodiment of the invention.

FIG. 17 shows, in partial cross section, an inflatable/deflatable suction cup design using a skin and web construction, according to an embodiment. This can be molded using the "lost wax" method, which is known to those of ordinary skill in the art. FIG. 18 shows the wax core (96) that would be placed in the mold to produce the structure in FIG. 17.

Figure 19:
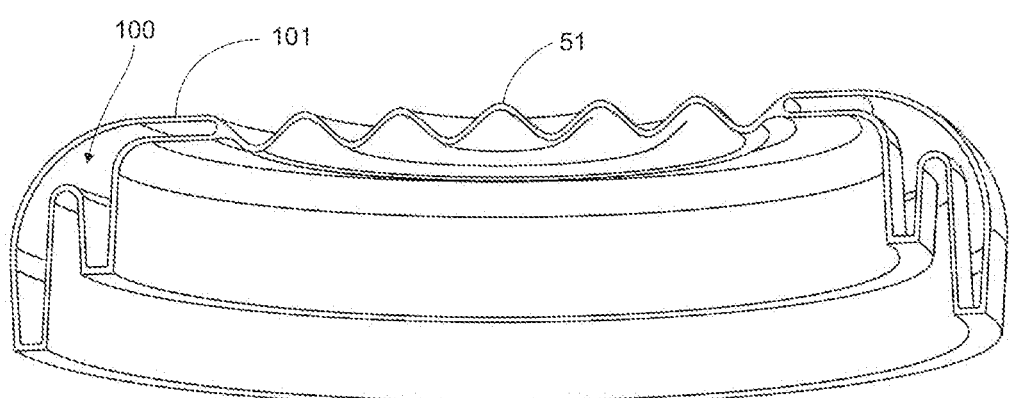
FIG. 19 is an illustration of an inflatable/collapsible skin structure to be filled with open-cell foam, according to an embodiment of the invention.

FIG. 19 shows, in cross section, an inflatable/deflatable suction cup design, according to an embodiment. The suction cup design has a skin (101) enclosing a space that would be filled with an open cell foam (such as a polyurethane foam). The fibrils that comprise the foam are bonded to the skin (101), and span the empty space so the suction cup will maintain its shape when it is pressurized with a fluid (e.g., with saline solution). When the space within the foam is evacuated, the suction cup collapses to a small cross section under the pressure of the surrounding atmosphere.

Figure 20:
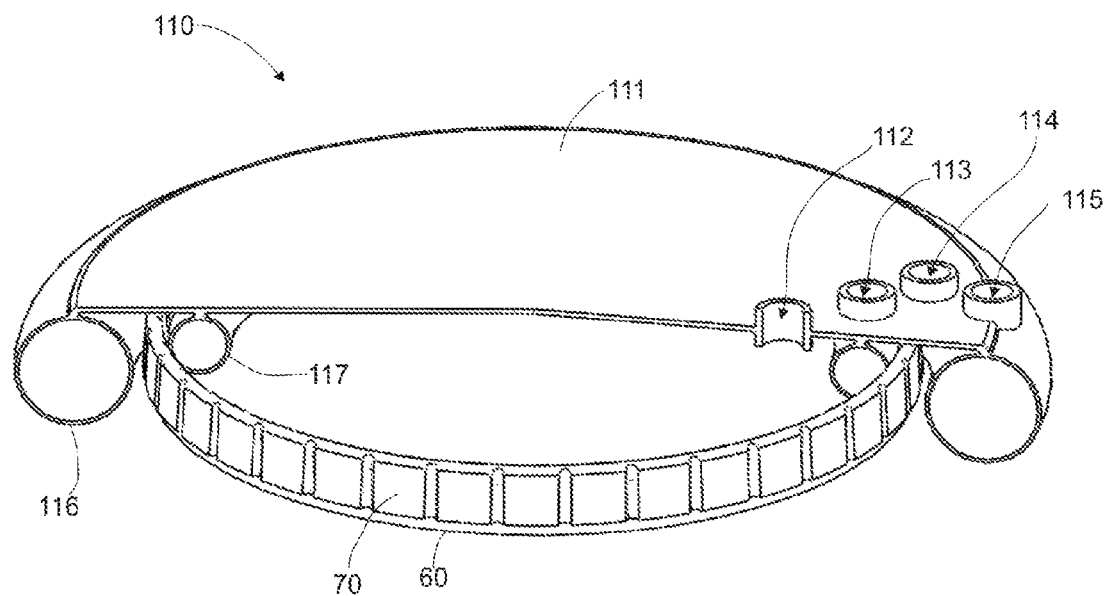
FIG. 20 is an illustration of the geometry for the inflatable structure with minimum material, according to an embodiment of the invention.

FIG. 20 shows an inflatable/deflatable suction cup design, according to an embodiment. This design uses simpler geometric elements (e.g., circular cross-section tubes) that do not need any internal webs or open cell foam to keep their shape under pressure. Port (112) provides for suction to the inner chamber. Port (114) provides for suction to the outer chamber. Ports (113, 115) will connect to the same tube which supplies fluid (e.g., water or air) to inflate or deflate the structure. The cutting element support ring (70) can be attached to the suction cup by a very small amount of glue (such as clear silicone II RTV sealant, from GE®). The cutting element (60) can be over-molded by the support ring, or can be glued to it.

Figure 21:
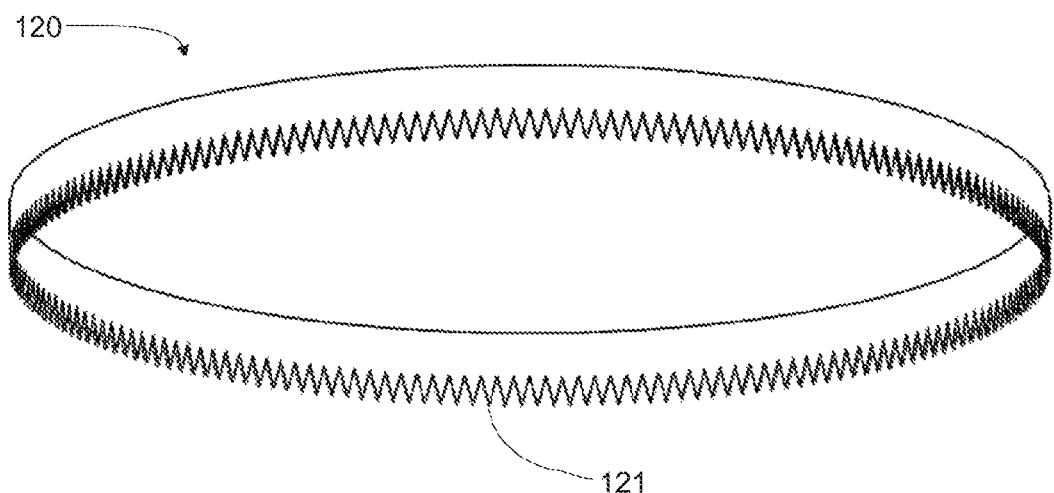
FIG. 21 is an illustration of a toothed ring for mechanical cutting, according to an embodiment of the invention.
Figure 22:
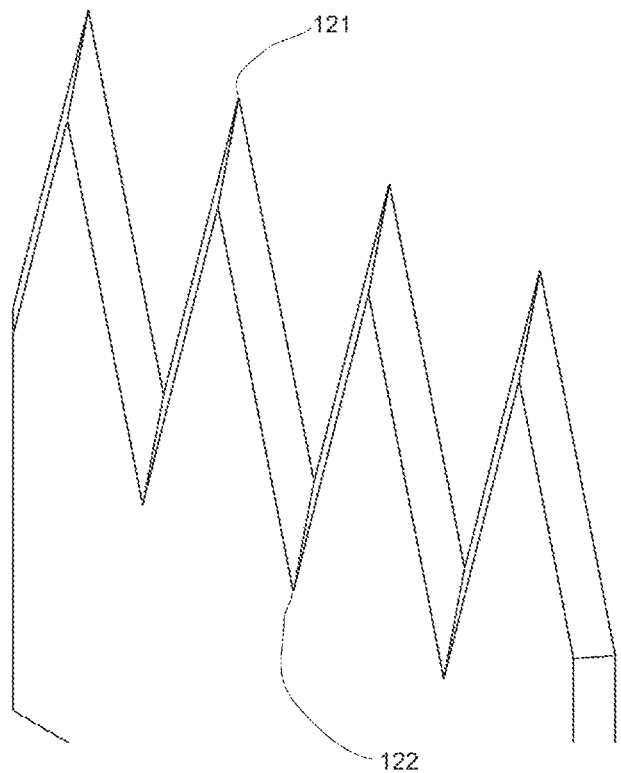
FIG. 22 is a close-up view of the sharp microteeth of the device, according to an embodiment of the invention.

FIG. 21 shows a mechanical cutting element (120) with ultrasharp microteeth (121), according to an embodiment. This embodiment includes two hundred of the teeth, though the number can vary with different designs. FIG. 22 shows a close-up view of a few teeth, according to an embodiment. The teeth can be made by photoetching sheet metal, such as 12.5 micron thick stainless steel, from one side and stopping the etch shortly after it breaks through to the other side.

Figure 23:
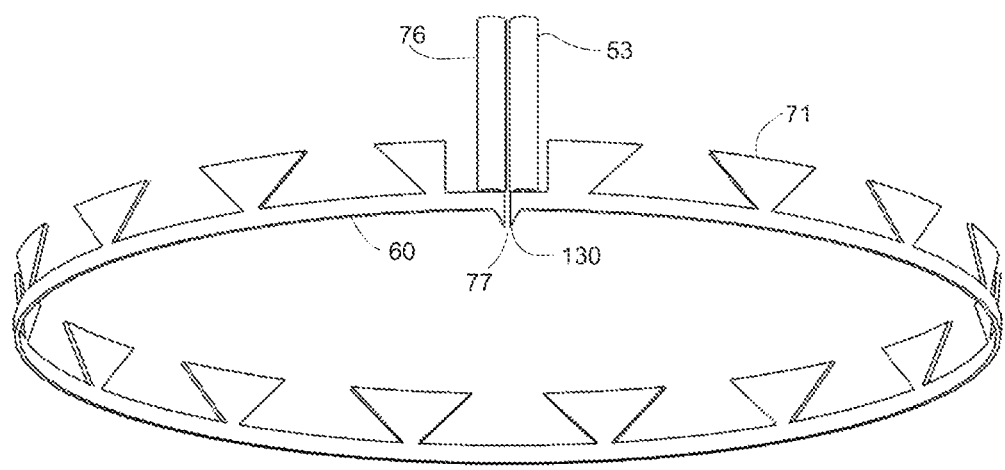
FIG. 23 is an illustration of an electromechanical cutting element having a single tooth, according to an embodiment of the invention.

FIG. 23 shows an electromechanical cutting element having one tooth (130), according to an embodiment. As in all the other embodiments, the capsule does not contact the cutting element until after the suction has been turned on for the outer chamber (which does not occur until after suction has already been applied in the inner chamber). The capsule is anchored by the inner chamber, so it does not shift position as suction builds up in the outer chamber. It simply develops a bulge that extends into the depth of the outer chamber, and the cutting element contacts the membrane in a perpendicular manner. In this case, the tooth contacts the membrane, and punctures it. That starts a tear which can be completed by the pulse of steam that will be generated by the electrical discharge.

Figure 24:
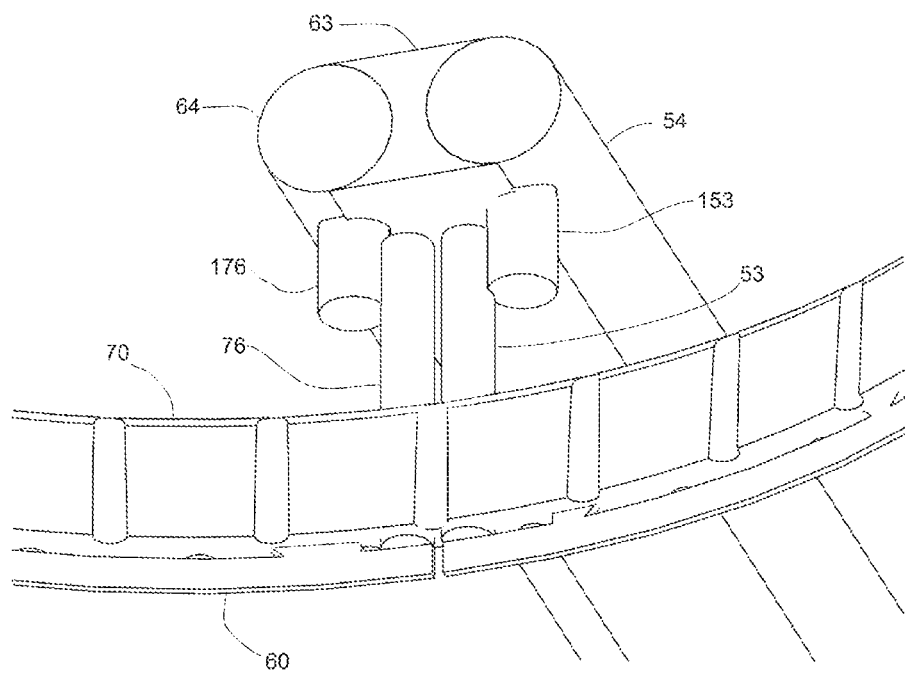
FIG. 24 is a close-up view of the electrical connections to the electrical cutting element, according to an embodiment of the invention.

FIG. 24 shows a close-up view of the electrical connections to the electrical cutting element, according to an embodiment. The electrical cutting element (60) is mechanically held by the plastic support ring (70) that may be molded over it (enclosing tabs 71) or glued to tabs (71) (ring 70 is in turn glued into the suction cup). The electrical cutting element is spot welded (e.g., by e-beam or laser welding) to leads (53, 76) which in turn are spot welded to pins (153, 176), which are mechanically pressed into holes in wires (54, 64), which are mechanically held together by insulation (63) (which may be epoxy).

Disposable Unit

Figure 25:
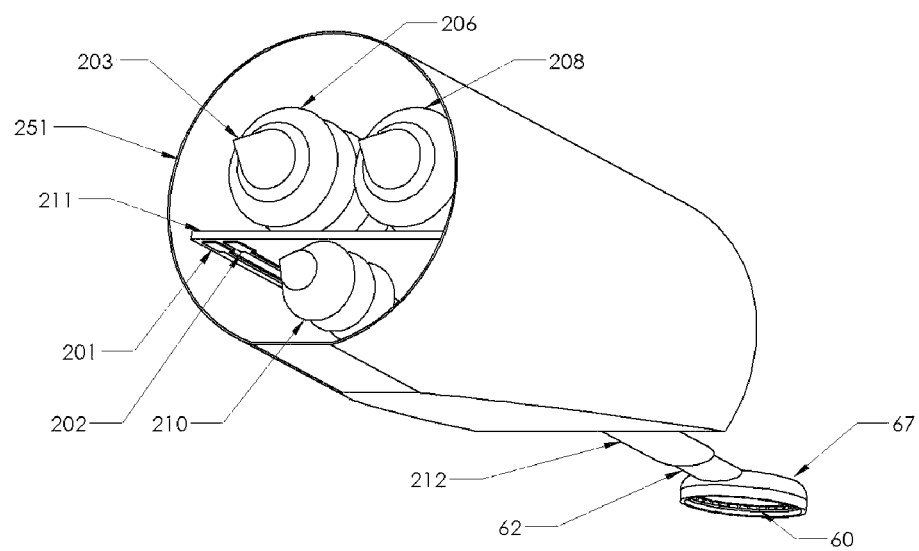
FIG. 25 is a rear view of the microsurgery/capsulotomy device with a disposable unit, according to an embodiment of the invention.
Figure 26:
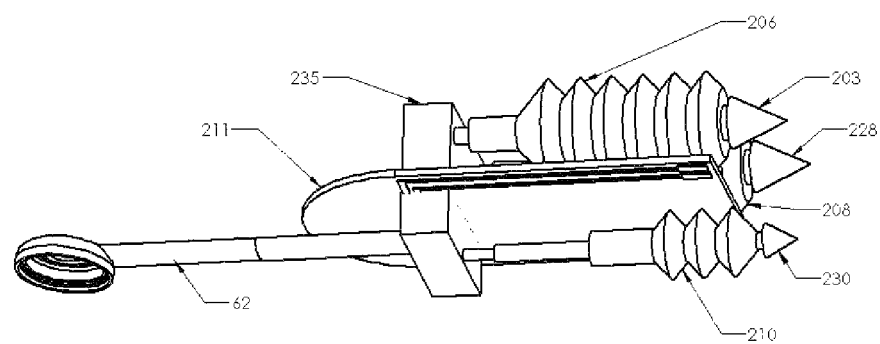
FIG. 26 is a side view of the internal components of the device with the disposable unit, according to an embodiment of the invention.
Figure 27:
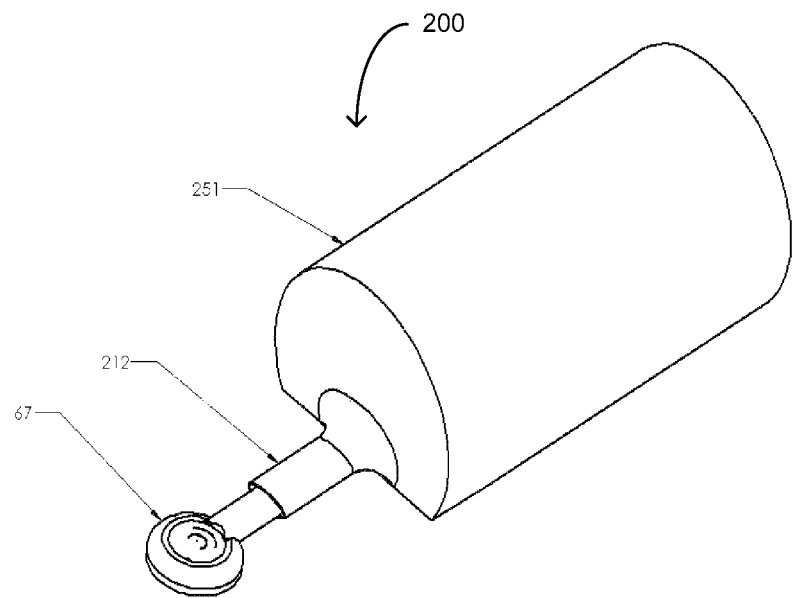
FIG. 27 is a top view of the device with the disposable unit, according to an embodiment of the invention.
Figure 28:
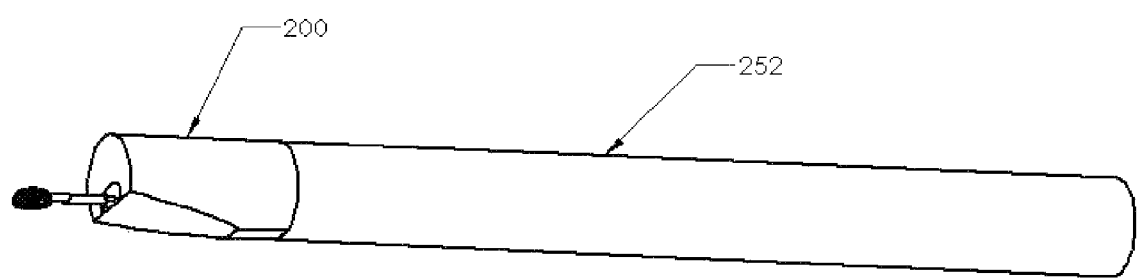
FIG. 28 is a side view of the device with the disposable unit attached to the reusable handpiece, according to an embodiment of the invention.

FIGS. 25-27 show the entire disposable unit (200) and FIG. 28 shows the disposable unit (200) attached to the handpiece (252), according to an embodiment. FIGS. 25-27 illustrate the housing (251) of the unit (200), the insertion tube (212) that is incorporated into the unit (200) design, the stem/arm (62), the suction cup (67), and the underside of the suction cup (67) that includes a cutting element (60). The suction cup (67), stem (62), and cutting element (60) were described in detail above. The housing (251) is typically composed of plastic, though it can alternatively be composed of other materials (e.g., metal, etc.).

FIG. 25 illustrates a rear view the unit (200) of the microsurgery/capsulotomy device including a back view of some of the internal components of the unit (200). In FIG. 26, the housing (251) is removed to show the internal components. The insertion tube (212) is an integral part of the housing (251) so it has also been removed in FIG. 26 to show the underlying internal features. The disposable unit provides a closed sterile system that does not introduce any contamination to the patient or transmit any contamination from the patient to the reusable handpiece (252), which is shown in FIG. 28. FIGS. 25 and 26 illustrate bellows (206, 208) inside the unit. Any fluid removed from the patient (e.g., fluid from inside the eye) will be trapped in these bellows (206, 208). Fluid flow is produced by pushing or pulling on closed bellows (206, 208, and 210). In some embodiments, the bellows (206, 208, and 210) are composed of plastic, though other materials can also be used (e.g., elastomeric materials, flexible metals, etc.).

To use the unit, the surgeon will grip the housing (251) and plug it into a non-disposable (reusable) handpiece (252) (FIG. 28) such that the conical mechanical connectors (203, 228, 230) engage latching grippers (not shown). The grippers can be moved by electric motors during the operation as needed to compress or expand the bellows. Bellows (206) has fluidic communication with the outer chamber of the suction cup, bellows (208) connects to the inner chamber of the suction cup, and bellows (210) connects to the inflatable space (for inflatable suction cups). All fluidic connections can be made in the manifold (235) at the factory. All components can be mounted on the circuit board (211), and this circuit board ensemble can be moved as a unit with respect to the housing so that the suction cup can be pulled into the insertion tube (212), and pushed out of the insertion tube (212). In addition to the latching gripper mechanical connections, there are electrical contacts in the reusable part of the handpiece (252) that connect to electrical leads (201) and (202) on the circuit board (211) (for units having an electrical cutting element).

FIGS. 25-27 illustrate an example of a disposable unit for use with the invention. However, other unit designs can also be used. In some embodiments, the unit is a more simple structure, some or all of the internal components, bellows, etc. exist separate from the rest of the device. In the embodiment described above, the insertion tube (212) can also be a separate structure.

Figure 29A:
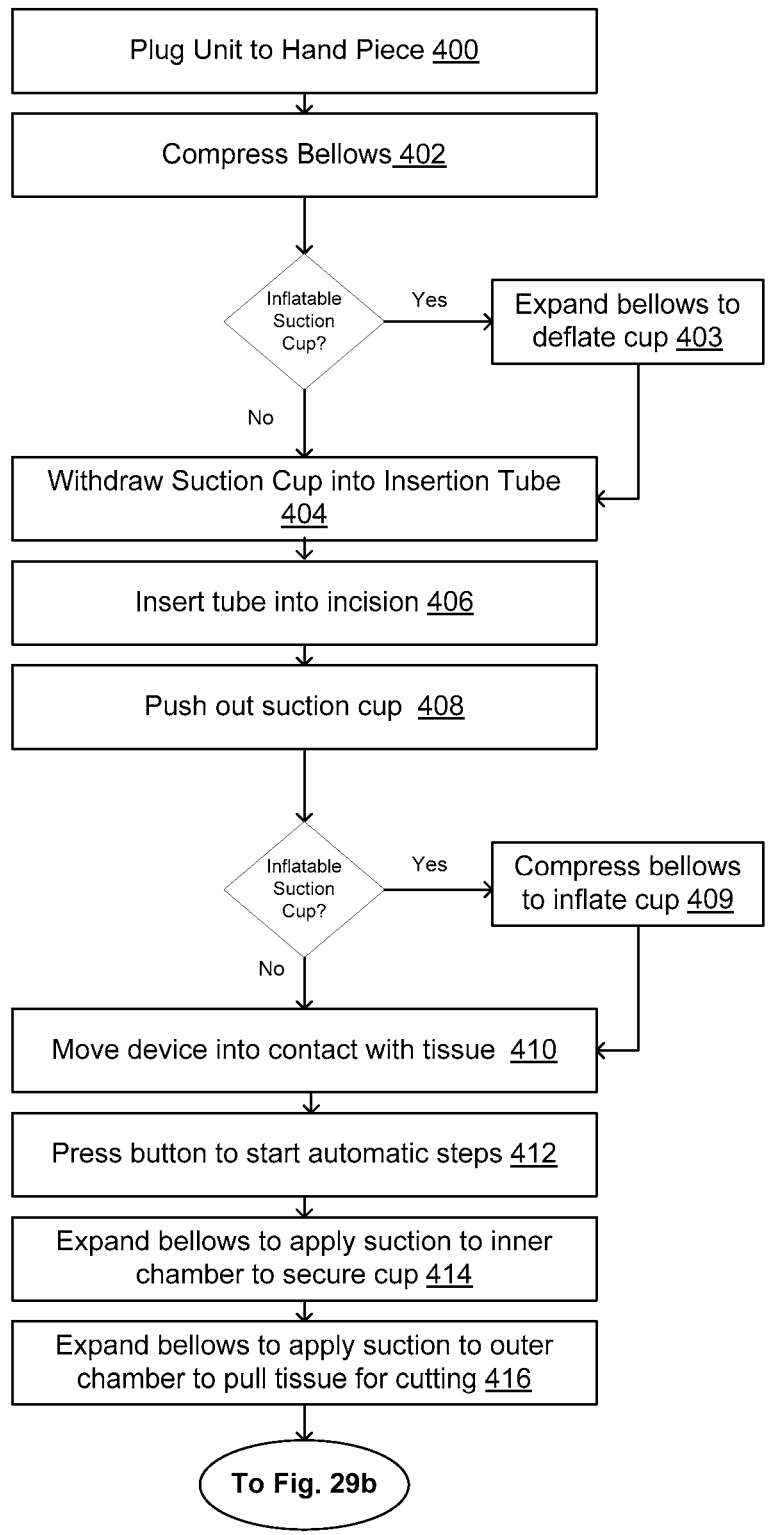
FIG. 29a is a flow chart illustrating the microsurgery/capsulotomy procedure, according to an embodiment of the invention.

Referring now to FIGS. 29a and b, the procedure for use of the unit 200 in a microsurgery/capsulotomy procedure is shown, according to an embodiment. The procedure includes opening the sterile package containing the disposable unit (200). It is stored in the extended position with the suction cup (67) outside the insertion tube (212) to ensure that the elastomer does not take a set. The unit is plugged (400) into a reusable handpiece (252), as described above and as illustrated in FIG. 28. Bellows (206) and (208) are then fully compressed (402) to their minimum volume. For an inflatable-type suction cup, the inflating liquid is sealed into the suction cup/bellows (210) system at the factory. So, optionally, the surgeon can expand (403) the bellows to make the suction cup deflate in an inflatable embodiment. The surgeon can next pull/withdraw (404) the suction cup (67) into insertion tube (212) by a motor that moves the entire circuit board ensemble back relative to housing (251). The surgeon then inserts (406) the insertion tube tip into a corneal incision created by the surgeon. The circuit board ensemble is moved forward relative to the housing (251) to push (408) the suction cup (67) out. The friction in the insertion tube (212) should be kept as low as possible (e.g., by choice of materials and lubrication). Optionally, bellows (210) is compressed (409) by an electric motor to inflate the suction cup (if it is an inflatable type). The surgeon moves (410) the device to the lens capsule, centers the ring over the optic axis of the lens, and brings it into contact with the lens capsule.

In one embodiment, the surgeon presses (412) a button that executes the rest of the capsulotomy operation automatically under the control of an embedded microcontroller in the handpiece (252). The controller turns on the electric motor that expands (414) bellows (208) to produce suction in the inner chamber of the suction cup. The suction pulls tissue into the inner chamber to secure the suction cup in place. The suction pressure can be measured by the motor current, and the fluid flow into the bellows can be measured by the rotational position of the motor shaft as a function of time. When the controller determines that the desired suction pressure and a sufficiently leak tight seal have been achieved, it will turn on the electric motor that expands (416) bellows (206), which applies suction to the outer chamber of the suction cup (67).

Figure 29B:
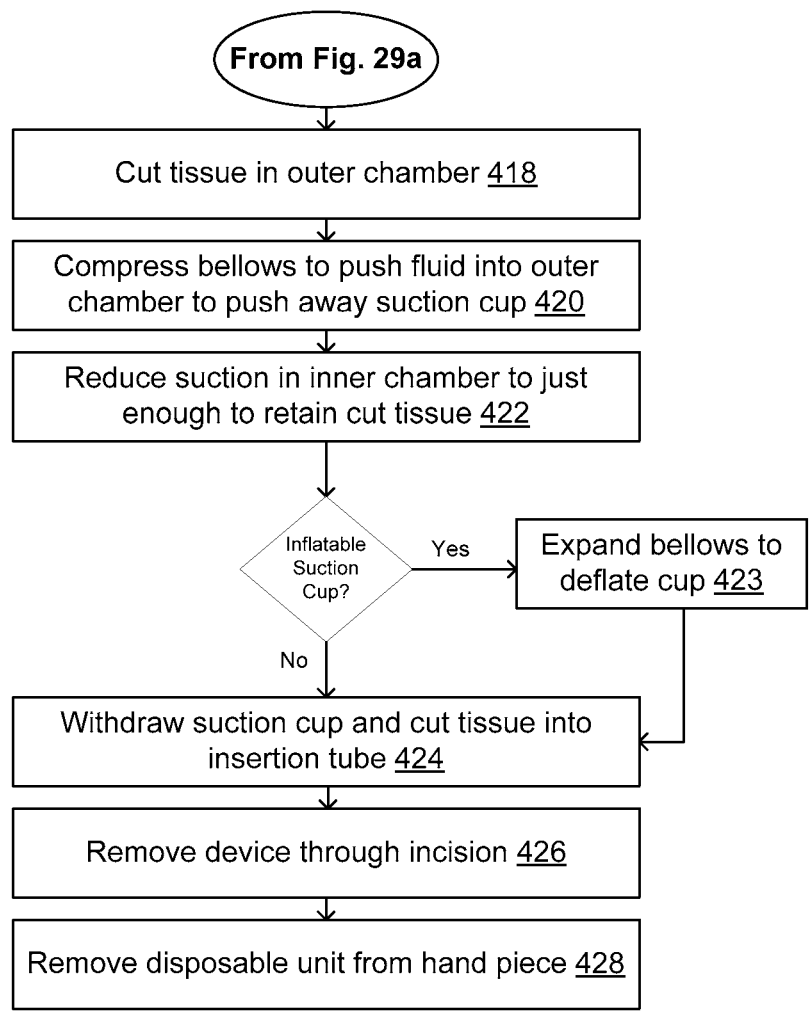
FIG. 29b is a continuation of the flow chart of FIG. 29a illustrating the microsurgery/capsulotomy procedure, according to an embodiment of the invention.

Moving on to FIG. 29b, this Figure shows a continuation of the procedure of 29a. The suction pulls tissue into the outer chamber for cutting (418) the tissue. Once it is determined that the desired suction pressure has been achieved in the outer chamber, then either an electrical discharge occurs to cut (418) the tissue (for the electrical cutting element type), or the cut (418) will be finished mechanically (for the mechanical cutting element type). Then, bellows (206) is compressed (420) to release suction to the outer chamber and to push fluid into the outer chamber to push the lens away from the suction cup (67). Suction in the inner chamber is reduced (422) until there is just enough to retain the cut patch of membrane there. Optionally, bellows (210) is expanded (423) (for inflatable suction cups) to deflate the suction cup (67) (for inflatable suction cup). The suction cup (67) and the cut patch of membrane are pulled (424) into insertion tube (212) and the insertion tube (212) is pulled out of/removed (426) from the corneal incision. The disposable unit is pulled off of/removed from (428) the reusable handpiece (252) and thrown away.

The reusable handpiece (252) can take on a variety of forms, and FIG. 28 illustrates just one example. In one embodiment, the handpiece (252) is a battery powered unit having an embedded microcontroller, a reversible electric motor for each bellows, and an electric motor to move the circuit board ensemble. For electrical cutting elements, the handpiece (252) will contain a capacitor.

Although bellows (206) and (208) can accommodate only a limited volume of total flow, it is far more than needed to do the job. The volume of the bellows can be, for example, 10 milliliters when fully expanded, while the total fluid sucked from the eye should be less than 1 ml. Normally there will be another fluidic line inserted into the eye to inject or withdraw fluid as needed to maintain the correct internal volume of the anterior chamber throughout the course of the operation. It is possible to incorporate such a make-up line into the device of the invention, if desired.

As noted above, the devices and procedures described in this application can be used in performing lens capsule surgery (e.g., for cataract treatment, for implantation of an IOL, or other treatments in which creation of an opening in the lens capsule is desired). As explained above, the devices and procedures described here are not limited to lens capsule surgery, but can also be useful in other treatments of the eye, such as a corneal surgery, treatments for glaucoma, microfinestration of the optic nerve, surgeries involving decemet's membrane, among others. In these types of applications, the procedures and devices function in generally the same manner as described above regarding the lens capsule surgery. In addition, the devices and procedures may be useful for performing other medical procedures outside of the eye, such as procedures involving fenestration of brain dura, and others. In these types of applications, the procedures and devices function in generally in the same manner as described above regarding the lens capsule surgery. The devices for these surgeries might look a bit different because they have to fit into differently-shaped organs, but the cutting mechanism would use the same ideas.

EXAMPLES

A number of prototype designs were built and tested on lenses from rabbit eyes. The cutting elements were made by photochemical etching 302 stainless steel full hardness sheet foil 25 microns thick. The isotropic etching was done from one side to produce a beveled edge as indicated in FIG. 22. Capsulotomies were successfully performed with electrical cutting elements having cross sections of 25 microns×50 microns, and resistances of 4 to 6 ohms, with the electrical discharge from a 90 microfarad foil capacitor with initial voltage of 70 V and final voltage of 0 V. The cutting element was observed to flash a bright yellow color, which corresponds to a temperature of about 1000° C. Successful suction cups were molded from silicone MED-6015, MED4-4220 (from NUSIL, INC.®), and from TAP silicone RTV (from TAP PLASTICS®). The discharge times were less than 1 millisecond. Shorter discharge times could be achieved by increasing the initial voltage (e.g., 400 V), and/or decreasing the cutting element resistance (e.g., 1-2 ohms). The total energy needed to heat the steel cutting element and the trapped layer of water was about 0.2 joules. This amount of energy would be released from a 90 microfarad capacitor going from 400V to 394V. This corresponds to a 3% discharge, so only a small fraction of the RC time constant is needed. One way to stop the discharge at this point is to design the cutting element to melt and break the circuit upon dissipating the desired quantity of energy. Another way is to use an electronic control circuit. A discharge of 0.2 joules in 10 microseconds corresponds to a power of 20 kW. The total amount of energy is too small to damage the surrounding tissue as the heat is conducted away over the next several milliseconds.

Prototype mechanical cutting elements were also made by one-sided photochemical etching of stainless steel full hard foil 25 microns thick. The largest number of teeth tried was 72, and this made successful capsulotomies in rabbit eye lenses when a suction of 7 inches of mercury, or more, was applied to the silicone suction cup.

The above description is included to illustrate the operation of the embodiments and is not meant to limit the scope of the invention. The scope of the invention is to be limited only by the following claims. From the above discussion, many variations will be apparent to one skilled in the relevant art that would yet be encompassed by the spirit and scope of the invention. As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

I claim:

1. A method of performing a capsulotomy of a lens capsule of an eye, the method comprising:
  inserting a conductive heating, circular cutting element of a capsulotomy device through an incision in a cornea of the eye, the cutting element being mounted to an underside of a suction cup of the capsulotomy device and collapsible for insertion through the incision to access the lens capsule, the cutting element further designed to return to a pre-insertion shape following insertion into the eye through the incision;
  positioning the cutting element at the lens capsule;
  applying suction to the suction cup to secure the capsulotomy device to the lens capsule of the eye; and
  delivering one or more electrical pulses of energy to the cutting element for conductive heating of the cutting element to cut tissue of the lens capsule to allow removal from the eye of a patch of the tissue from the lens capsule, wherein a total duration of the one or more electrical pulses is 500 milliseconds or less.

2. The method of claim 1, wherein delivering one or more electrical pulses comprises delivering a plurality of electrical pulses to the cutting element, each pulse of energy separated by a period of time during which reduced or no electrical current is delivered to the cutting element, and wherein a total amount of energy delivered to the cutting element by the one or more electrical pulses is a sum of energy from each of the electrical pulses.

3. The method of claim 1, wherein delivering one or more electrical pulses further comprises delivering, by the one or more electrical pulses, a total amount of energy to the cutting element that does not exceed four joules.

4. The method of claim 1, wherein delivering one or more electrical pulses further comprises delivering, by the one or more electrical pulses, a total amount of energy to the cutting element that does not exceed two joules.

5. The method of claim 1, wherein delivering one or more electrical pulses further comprises delivering one or more electrical pulses in which the total duration of the one or more electrical pulses is 50 milliseconds or less.

6. The method of claim 1, wherein delivering one or more electrical pulses further comprises delivering one or more electrical pulses in which the total duration of the one or more electrical pulses is 10 milliseconds or less and total amount of energy delivered to the cutting element by the one or more electrical pulses does not exceed two joules.

7. The method of claim 1, wherein delivering one or more electrical pulses further comprises delivering one or more electrical pulses according to parameters that result in producing steam at the cutting element, the steam expanding to increase tensile stress in the tissue for tearing the tissue to produce the patch of tissue for removal from the eye.

8. A method of performing a capsulotomy of a lens capsule of an eye, the method comprising:
    inserting a conductive heating, circular cutting element of a capsulotomy device through an incision in a cornea of the eye, the cutting element being mounted to an underside of a suction cup of the capsulotomy device and collapsible for insertion through the incision to access the lens capsule, the cutting element further designed to return to a pre-insertion shape following insertion into the eye through the incision;
    positioning the cutting element at the lens capsule;
    applying suction to the suction cup to secure the capsulotomy device to the lens capsule of the eye; and
    delivering one or more electrical pulses of energy to the cutting element for conductive heating of the cutting element to cut tissue of the lens capsule to allow removal from the eye of a patch of the tissue from the lens capsule, wherein a total amount of energy delivered to the cutting element by the one or more electrical pulses does not exceed four joules of energy.

9. The method of claim 8, wherein delivering one or more electrical pulses comprises delivering a plurality of electrical pulses to the cutting element, each pulse of energy separated by a period of time during which reduced or no electrical current is delivered to the cutting element, and wherein a total amount of energy delivered to the cutting element is a sum of energy from each of the electrical pulses.

10. The method of claim 8, wherein delivering one or more electrical pulses further comprises delivering a total amount of energy to the cutting element that does not exceed two joules.

11. The method of claim 8, wherein delivering one or more electrical pulses further comprises delivering a total amount of energy to the cutting element that does not exceed 0.2 joules.

12. The method of claim 8, wherein delivering one or more electrical pulses further comprises delivering one or more pulses in which a total duration of the one or more electrical pulses is 50 milliseconds or less.

13. The method of claim 8, wherein delivering one or more electrical pulses further comprises delivering one or more pulses in which a total duration of the one or more electrical pulses is 1 millisecond or less.

14. The method of claim 8, wherein delivering one or more electrical pulses further comprises delivering one or more electrical pulses in which a total duration of the one or more electrical pulses is 5 milliseconds or less and the total amount of energy delivered to the cutting element does not exceed two joules.

15. The method of claim 8, wherein delivering one or more electrical pulses further comprises delivering one or more electrical pulses according to parameters that result in producing steam at the cutting element, the steam expanding to increase tensile stress in the tissue for tearing the tissue to produce the patch of tissue for removal from the eye.

16. A method of performing a capsulotomy of a lens capsule of an eye, the method comprising:
    inserting a conductive heating cutting element of a capsulotomy device through an incision in a cornea of the eye, the cutting element being collapsible for insertion through the incision to access the lens capsule, the cutting element further designed to return to a pre-insertion shape following insertion into the eye through the incision;
    positioning the cutting element at the lens capsule; and
    delivering one or more electrical pulses of energy to the cutting element for conductive heating of the cutting element to cut tissue of the lens capsule to allow removal from the eye of a patch of the tissue from the lens capsule, the one or more electrical pulses delivered according to parameters that result in producing steam at the cutting element, the steam expanding to increase tensile stress in the tissue for tearing the tissue to produce the patch of tissue for removal from the eye, wherein a total duration of the one or more electrical pulses is 500 milliseconds or less.

17. The method of claim 16, wherein the cutting element is circular and is mounted to the underside of a suction cup, and wherein the method further comprises applying suction to the suction cup to secure the capsulotomy device to the lens capsule of the eye.

18. The method of claim 16, wherein the cutting element is circular and wherein delivering one or more electrical pulses comprises delivering a plurality of electrical pulses to the cutting element, each pulse of energy separated by a period of time during which reduced or no electrical current is delivered to the cutting element, and wherein a total amount of energy delivered to the cutting element by the one or more electrical pulses is a sum of energy from each of the electrical pulses.

19. The method of claim 16, wherein the cutting element is circular and wherein delivering one or more electrical pulses further comprises delivering, by the one or more electrical pulses, a total amount of energy to the cutting element that does not exceed four joules.

20. The method of claim 16, wherein the cutting element is circular and wherein delivering one or more electrical pulses further comprises delivering, by the one or more electrical pulses, a total amount of energy to the cutting element that does not exceed two joules.

21. The method of claim 16, wherein the cutting element is circular and wherein delivering one or more electrical pulses further comprises delivering one or more electrical pulses in which the total duration of the one or more electrical pulses is 1 millisecond or less.

22. The method of claim 16, wherein the cutting element is circular and wherein delivering one or more electrical pulses further comprises delivering one or more electrical pulses in which the total duration of the one or more electrical pulses is 5 milliseconds or less and a total amount of energy delivered to the cutting element by the one or more electrical pulses does not exceed two joules.

23. A method of performing a capsulotomy of a lens capsule of an eye, the method comprising:
inserting a conductive heating cutting element of a capsulotomy device through an incision in a cornea of the eye, the cutting element being collapsible for insertion through the incision to access the lens capsule, the cutting element further designed to return to a pre-insertion shape following insertion into the eye through the incision;
positioning the cutting element at the lens capsule; and
delivering one or more electrical pulses of energy to the cutting element for conductive heating of the cutting element to cut tissue of the lens capsule to allow removal from the eye of a patch of the tissue from the lens capsule, the one or more electrical pulses delivered according to parameters that result in producing steam at the cutting element, the steam expanding to increase tensile stress in the tissue for tearing the tissue to produce the patch of tissue for removal from the eye, wherein a total amount of energy delivered to the cutting element by the one or more electrical pulses does not exceed four joules of energy.

24. The method of claim 23, wherein the cutting element is circular and is mounted to the underside of a suction cup, and wherein the method further comprising applying suction to the suction cup to secure the capsulotomy device to the lens capsule of the eye.

25. The method of claim 23, wherein the cutting element is circular and wherein delivering one or more electrical pulses comprises delivering a plurality of electrical pulses to the cutting element, each pulse of energy separated by a period of time during which reduced or no electrical current is delivered to the cutting element, and wherein a total amount of energy delivered to the cutting element is a sum of energy from each of the electrical pulses.

26. The method of claim 23, wherein the cutting element is circular and wherein delivering one or more electrical pulses further comprises delivering a total amount of energy to the cutting element that does not exceed two joules.

27. The method of claim 23, wherein the cutting element is circular and wherein delivering one or more electrical pulses further comprises delivering a total amount of energy to the cutting element that does not exceed 0.2 joules.

28. The method of claim 23, wherein the cutting element is circular and wherein delivering one or more electrical pulses further comprises delivering one or more pulses in which a total duration of the one or more electrical pulses is 1 millisecond or less.

29. The method of claim 23, wherein the cutting element is circular and wherein delivering one or more electrical pulses further comprises delivering one or more pulses in which a total duration of the one or more electrical pulses is 10 milliseconds or less.

30. The method of claim 23, wherein the cutting element is circular and wherein delivering one or more electrical pulses further comprises delivering one or more electrical pulses in which a total duration of the one or more electrical pulses is 5 milliseconds or less and the total amount of energy delivered to the cutting element does not exceed two joules.

* * * * *